(12) United States Patent
Bouton et al.

(10) Patent No.: US 7,122,012 B2
(45) Date of Patent: Oct. 17, 2006

(54) DETECTION OF FLUIDS IN TISSUE

(75) Inventors: Chad Bouton, Delaware, OH (US);
Alan D. Hirschman, Glenshaw, PA (US)

(73) Assignee: MEDRAD, Inc., Indianola, PA (US)

( * ) Notice: Subject to any disclaimer, the term of this patent is extended or adjusted under 35 U.S.C. 154(b) by 116 days.

(21) Appl. No.: 10/206,390

(22) Filed: Jul. 26, 2002

(65) Prior Publication Data

US 2003/0036713 A1 Feb. 20, 2003

Related U.S. Application Data

(60) Provisional application No. 60/308,012, filed on Jul. 26, 2001.

(51) Int. Cl.
*A61B 5/117* (2006.01)
*A61B 5/103* (2006.01)

(52) U.S. Cl. ..................................................... 600/587
(58) Field of Classification Search ................ 600/587, 600/407, 547, 382, 384, 393, 430, 534, 595; 128/DIG. 13; 604/49–52, 116; 343/100, 343/718, 755, 757; 378/51
See application file for complete search history.

(56) References Cited

U.S. PATENT DOCUMENTS

| | | |
|---|---|---|
| 3,779,079 A | 12/1973 | Snook |
| 3,951,136 A | 4/1976 | Wall |
| 4,010,749 A | 3/1977 | Shaw |
| 4,240,445 A | 12/1980 | Iskander et al. |
| 4,329,689 A | 5/1982 | Yee |
| 4,378,808 A | 4/1983 | Lichtenstein |
| 4,488,559 A | 12/1984 | Iskander |
| 4,572,182 A | 2/1986 | Royse |
| 4,575,705 A | 3/1986 | Gotcher |
| 4,641,659 A | 2/1987 | Sepponen |
| 4,647,281 A | 3/1987 | Carr |

(Continued)

FOREIGN PATENT DOCUMENTS

DE 40 07 587 9/1991

(Continued)

OTHER PUBLICATIONS

Carr, K. L., "Use of Gallium Arsenide in Medical Applications," IEEE Gallium Arsenide Integrated Circuits (GAAS IC) Symposium, vol. SYMP 17, pp. 10-13, New York (Oct. 29, 1995).

(Continued)

*Primary Examiner*—Max F. Hindenburg
*Assistant Examiner*—Brian Szmal
(74) *Attorney, Agent, or Firm*—Gregory L. Bradley; Henry E. Bartony, Jr.

(57) ABSTRACT

A method of detecting a change (that is, an increase or a decrease) in the level of fluid in tissue in a first area of a body includes the steps of: applying electromagnetic energy, preferably in the frequency range of approximately 300 MHz to approximately 30 GHz, to a first volume of the body; measuring a resultant or returned signal; comparing the signal to a reference signal to determine if the fluid level in the tissue has changed. In one embodiment, the method detects changes in the level of fluid in tissue of a body by applying electromagnetic energy to a first volume of the body over a period of time (for example, using an antenna or antennae); measuring a resultant signal or a signal returned from the tissue; and comparing the signal to a reference signal to determine if a level of fluid in the tissue has changed during the period of time.

83 Claims, 25 Drawing Sheets

U.S. PATENT DOCUMENTS

| | | | |
|---|---|---|---|
| 4,648,869 | A | 3/1987 | Bobo, Jr. |
| 4,653,501 | A | 3/1987 | Cartmell et al. |
| 4,667,679 | A | 5/1987 | Sahota |
| 4,690,149 | A | 9/1987 | Ko |
| 4,816,019 | A | 3/1989 | Kamen |
| 4,819,648 | A | 4/1989 | Ko |
| 4,877,034 | A | 10/1989 | Atkins et al. |
| 4,923,442 | A | 5/1990 | Seagall et al. |
| 4,959,050 | A | 9/1990 | Bobo, Jr. |
| 4,971,068 | A | 11/1990 | Sahi |
| 5,001,436 | A | 3/1991 | Scot et al. |
| 5,026,348 | A | 6/1991 | Venegas |
| 5,334,141 | A | 8/1994 | Carr et al. |
| 5,769,784 | A | 6/1998 | Barnett et al. |
| 5,861,019 | A | 1/1999 | Sun et al. |
| 5,947,910 | A | 9/1999 | Zimmet |
| 5,954,668 | A | 9/1999 | Uber, III et al. |
| 5,957,950 | A | 9/1999 | Mockros et al. |
| 5,964,703 | A | 10/1999 | Goodman et al. |
| 5,995,863 | A | 11/1999 | Farace et al. |
| 6,026,173 | A | 2/2000 | Svenson et al. |
| 6,061,589 | A | 5/2000 | Bridges et al. |
| 6,233,479 | B1 | 5/2001 | Haddad et al. |
| 6,332,087 | B1 | 12/2001 | Svenson et al. |
| 6,375,624 | B1 | 4/2002 | Uber, III et al. |
| 6,408,204 | B1 | 6/2002 | Hirschman |
| 6,425,878 | B1 | 7/2002 | Shekalim |
| 6,459,931 | B1 | 10/2002 | Hirschman |
| 2002/0040193 | A1 | 4/2002 | Hirschman |
| 2002/0172323 | A1* | 11/2002 | Karellas et al. ............... 378/51 |
| 2003/0004433 | A1 | 1/2003 | Hirschman |
| 2003/0036674 | A1 | 2/2003 | Bouton |

FOREIGN PATENT DOCUMENTS

| | | |
|---|---|---|
| GB | 2251080 | 6/1992 |
| JP | 11-57001 | 3/1999 |
| WO | WO 99/26685 | 6/1999 |
| WO | WO 99/26686 | 6/1999 |
| WO | WO 99/29356 | 6/1999 |
| WO | WO 01/08729 | 2/2001 |
| WO | WO 03/009752 | 2/2003 |

OTHER PUBLICATIONS

Shaeffer, J. et al., "Early Detection of Extravasation of Radiographic Contrast Medium," Radiology, vol. 184, No. 1, pp. 141-144 (Jul. 1992).

Shaeffer, J., "Detection of Extravasation of Antineoplastic Drugs by Microwave Radiometry," Cancer Letters, 31, pp. 185-291 (1986).

"MMIC Receiver for Water-Vapor Radiometer," NASA Tech. Briefs, 34, (Sep. 1993).

Arkin et al., "Recent Developments in Modeling Heat Transfer in Blood Perfused Tissues," IEEE Transactions on Biomedical Engineering, vol. 41, No. 2, pp. 97-107 (Feb. 1994).

Harris and Von Maltzahn, "Infusion Line Model for the Detection of Infiltration Extravasation and Other Fluid Flow Faults," IEEE Transactions on Biomedical Engineering, vol. 40, No. 2, pp. 154-162 (Feb. 1993).

Montreuil and Nachman, "Multiangle Method for Temperature Measurement of Biological Tissues by Microwave Radiometry," IEEE Transactions on Microwave Theory and Techniques, vol. 39, No. 7, pp. 1235-1238 (Jul. 1991).

Lin, J. C. et al., "Microwave Imaging of Cerebral Edema," Proceedings of the IEEE, vol. 70, No. 5, pp. 523-524 (May 1982).

Kramer, G. G. et al., "Dielectric Measurement of Cerebral Water Content Using a Network Analyzer," Neurological Research, vol. 14, No. 3, pp. 255-258 (Sep. 1992).

Ling, Geoffrey S. F. et al., "Diagnosis of Subdural and Intraparenchymal Intracranial Hemorrhage Using a Microwave Based Detector," Digitization of the Battlespace V and Battlefield Biomedical Technologies II, vol. 4037, pp. 212-217 (Apr. 24, 2000).

Behari, J., et al., "Dielectric Permittivity of Biological Tissues in the Microwave Frequency Range," Proceedings of the SPIE-The International Society for Optical Engineering, Advanced Microwave and Millimeter-Wave Detectors, vol. 2275, pp. 301-308, San Diego, CA (Jul. 25-26, 1994).

International Search Report for PCT Application No. PCT/US00/20112.

International Search Report for Counterpart PCT Application PCT/US02/23925.

International Search Report for PCT Application No. PCT/US02/23877.

Kent, M., Hand-Held Instrument for Fat/Water Determination in Whole Fish: Research paper from Distell Website; www.distell.com/index.php?exe=products:fish%20fat%20meter:research.

Lee, E. R., et al. "Body Conformable 915 MHz Microstrip Array Applicators for Large Surface Area Hyperthermia," IEEE Transactions on Biomedical Engineering, vol. 39, No. 5, pp. 470-483, IEEE Inc., New York (May 1, 1992).

Andreuccetti, D., et al., "High Permittivity Patch Radiator for Single and Multi-Element Hyperthermia Applicators," IEEE Transactions on Biomedical Engineering, vol. 40, No. 7, pp. 711-715, IEEE Inc., New York (Jul. 1, 1993).

U.S. Appl. No. 10/060,561, filed Jan. 30, 2002.

* cited by examiner

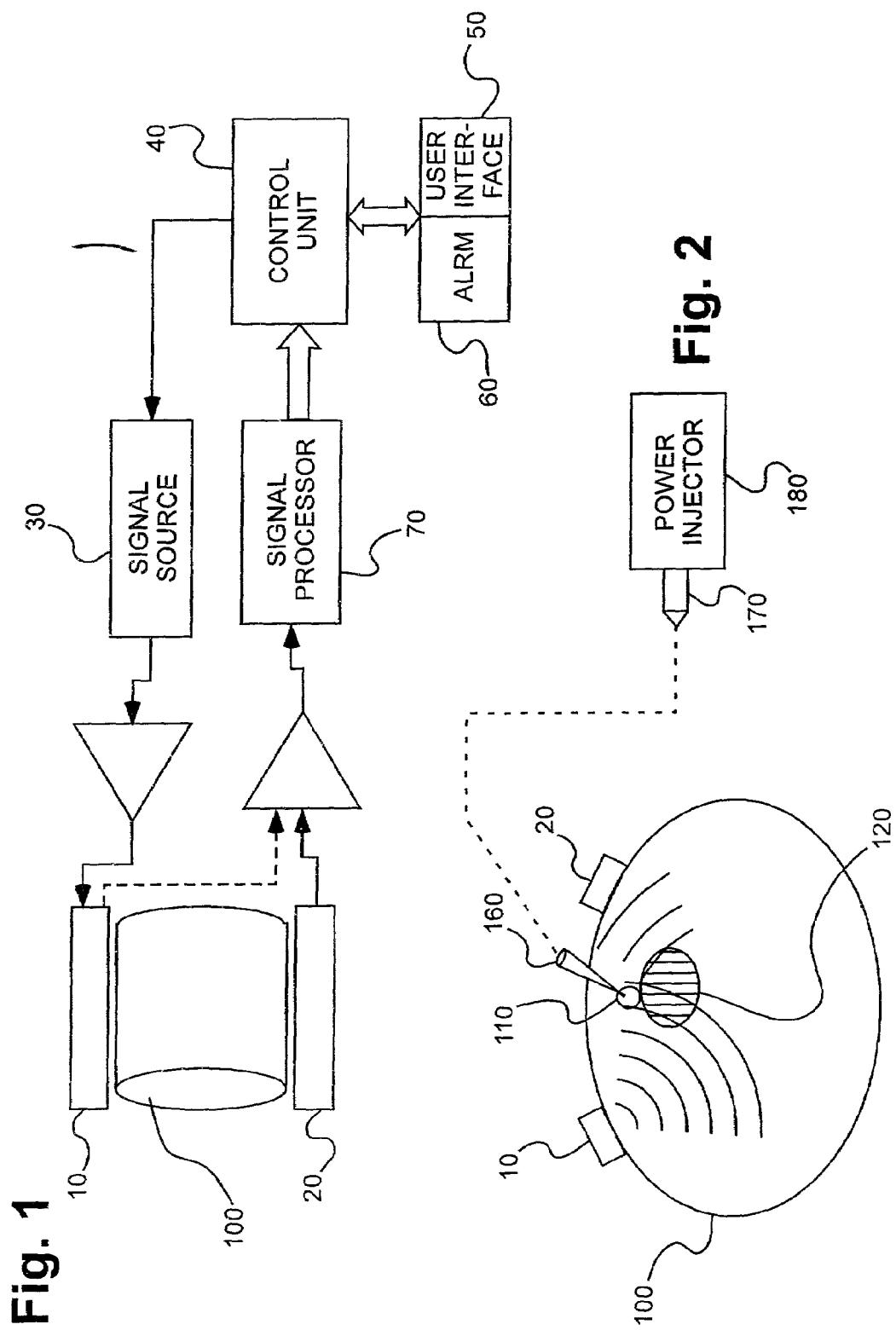

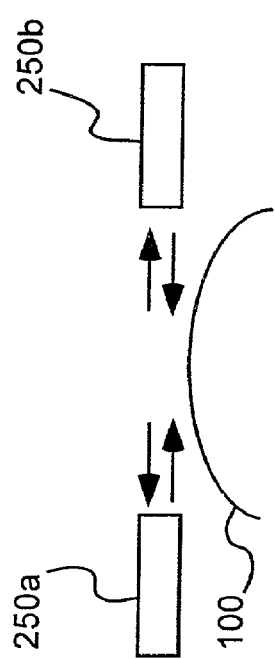
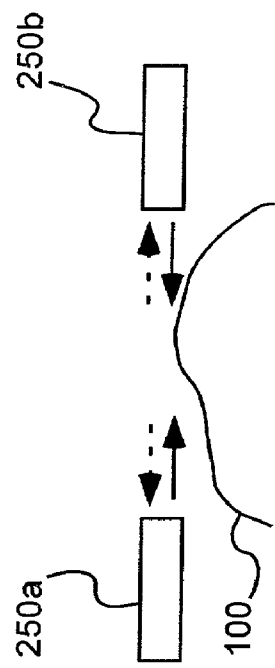
Fig. 4B
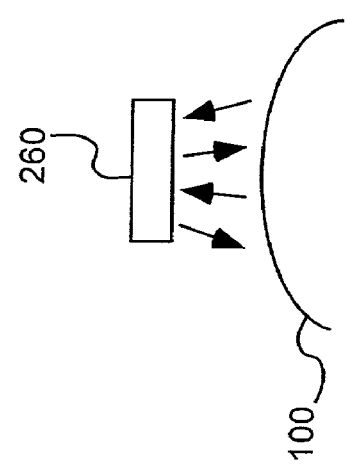
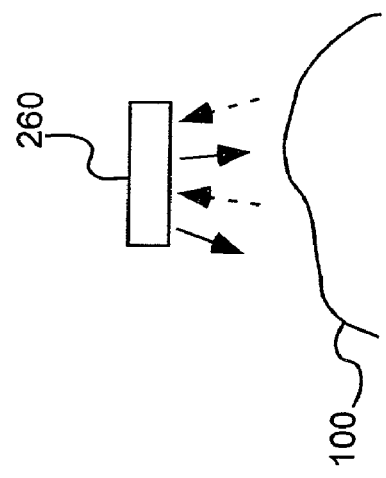
Fig. 4C

Fig. 19A
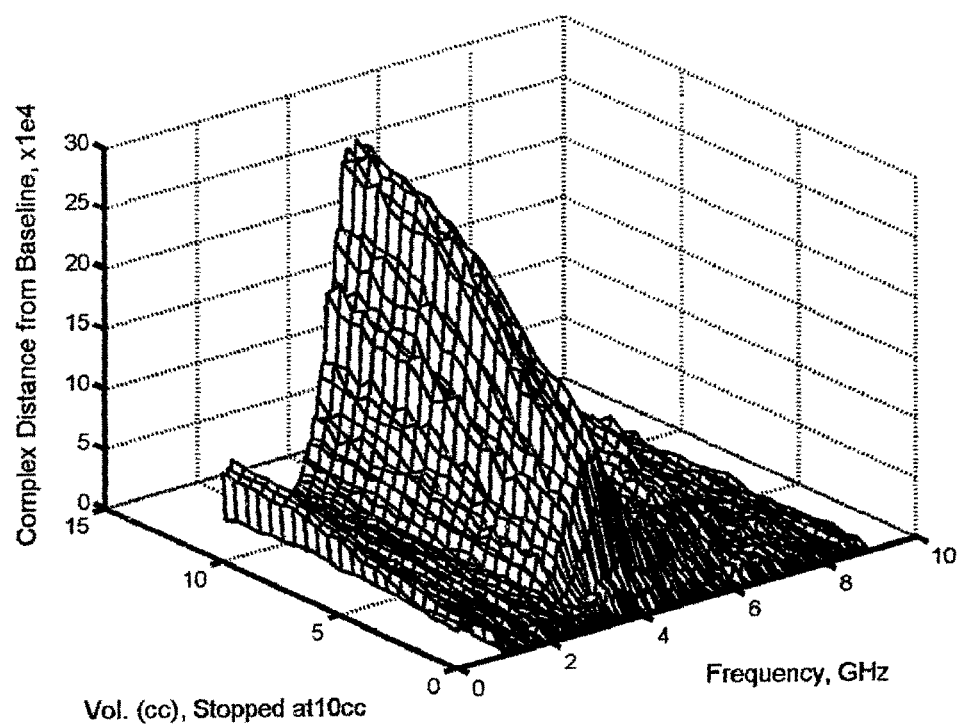
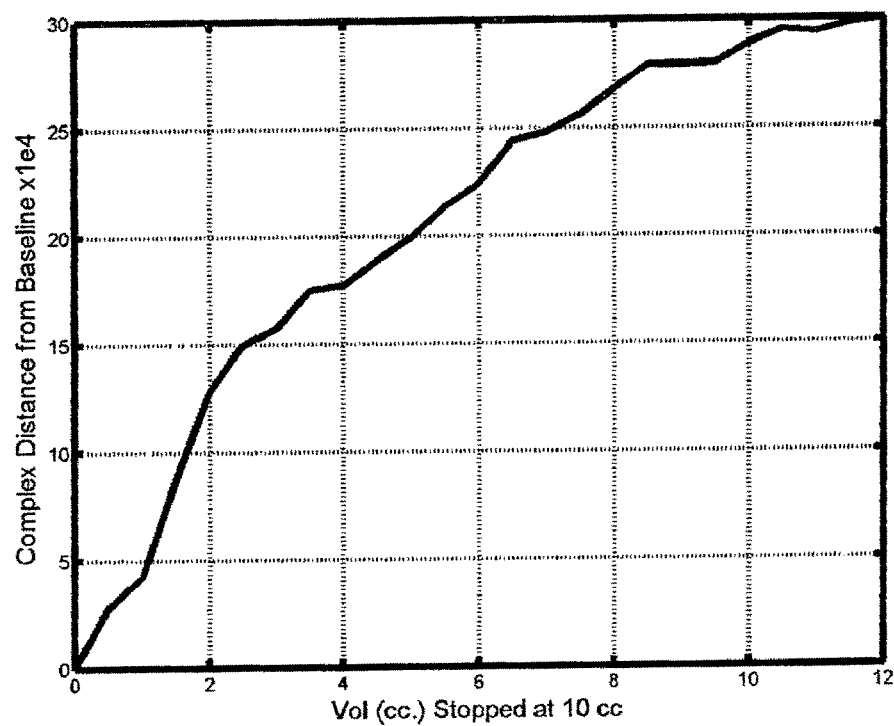

Fig. 19B
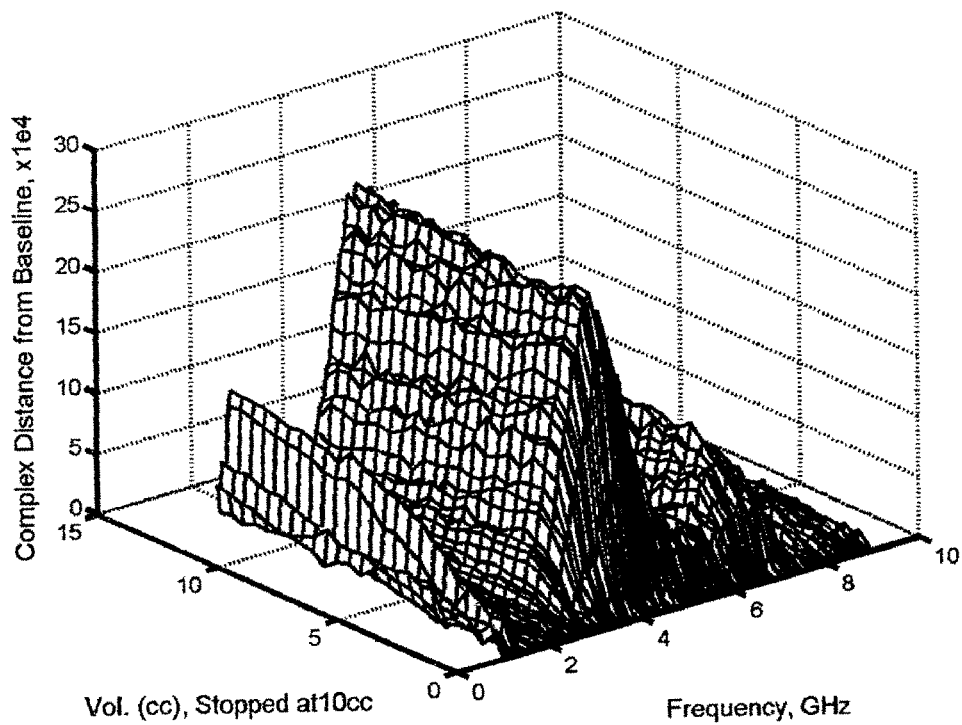
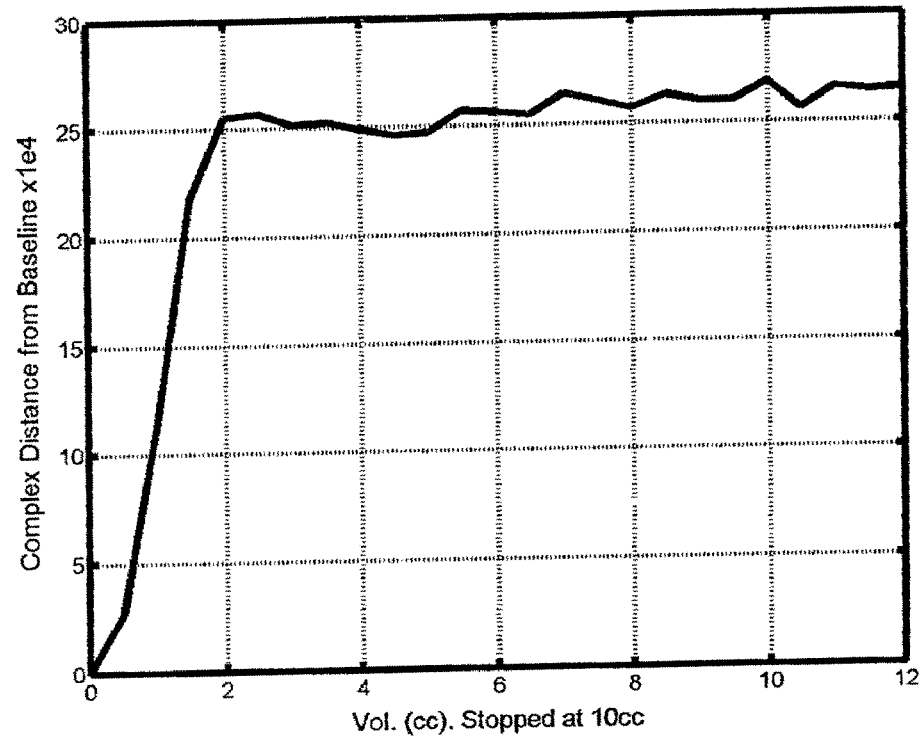

Fig. 19C
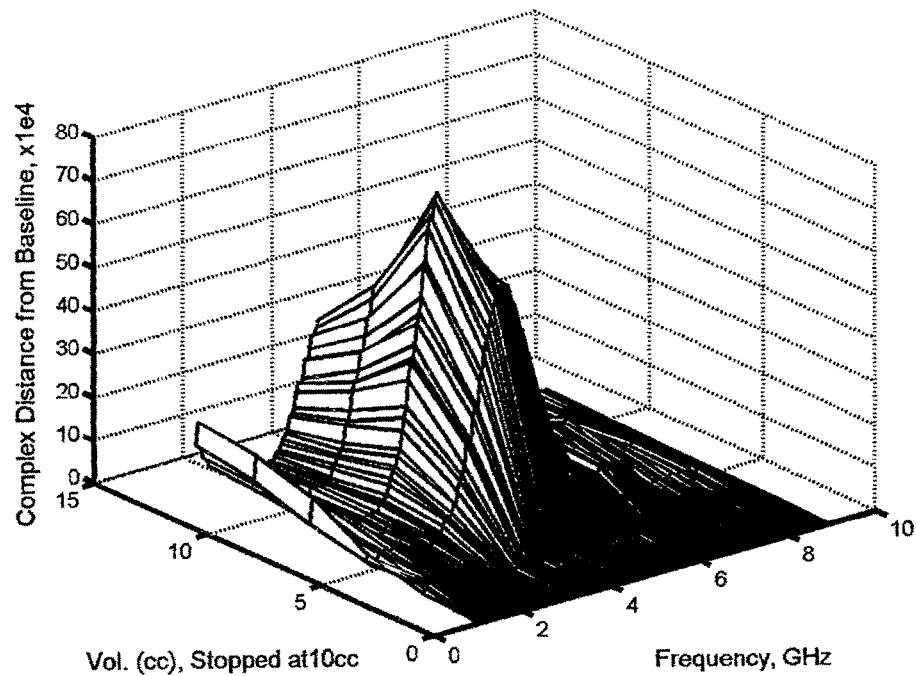
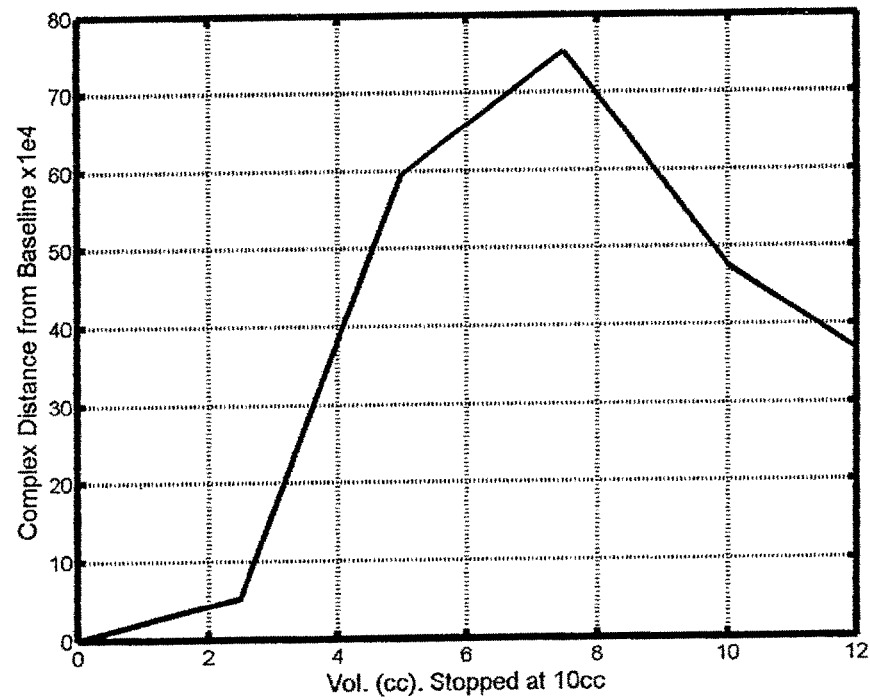

DETECTION OF FLUIDS IN TISSUE

CROSS-REFERENCE TO RELATED APPLICATIONS

This application claims the benefit of U.S. Provisional Patent Application Ser. No. 60/308,012, filed Jul. 26, 2001, the disclosure of which is incorporated herein by reference. This application is related to an application, filed on even date herewith, entitled ELECTROMAGNETIC SENSORS FOR BIOLOGICAL TISSUE APPLICATIONS AND METHODS FOR THEIR USE, also claiming priority to U.S. Provisional Patent Application Ser. No. 60/308,012, filed Jul. 26, 2001, the disclosure of which is also incorporated herein by reference.

BACKGROUND OF THE INVENTION

The present invention relates generally to the detection of fluids in tissue, and, more particularly, to apparatuses, systems and methods for detection of changed, elevated or abnormal fluid levels in tissue.

Changed, elevated or abnormal fluid levels in living tissue can result from a number of physiological conditions. For example, edema is an abnormal accumulation of watery fluid in the intercellular spaces of connective tissue. Edematous tissues are swollen and, when punctured, secrete a thin incoagulable fluid. Edema is most frequently a symptom of disease rather than a disease in itself, and it may have a number of causes, most of which can be traced back to gross variations in the physiological mechanisms that normally maintain a constant water balance in the cells, tissues, and blood. Among the causes may be diseases of the kidneys, heart, veins, or lymphatic system; malnutrition; or allergic reactions.

Moreover, bleeding (hemorrhage) can cause blood to collect and clot (hematoma). Hematomas can, for example, occur beneath the outermost of three membranes that cover the brain (meninges) as a result of a head injury. There are two types of cranial subdural hematomas. An acute subdural hematoma occurs soon after a severe head injury. A chronic subdural hematoma is a complication that may develop weeks after a head injury. Such a head injury may have been so minor that the patient does not remember it. An epidural hematoma is a traumatic accumulation of blood between the inner table of the skull and the stripped-off dural membrane. The inciting event often is a focused blow to the head. It is often difficult to detect hematomas, particularly when the hematoma occurs well after the time of an injury.

In addition to accumulation of body fluids, elevated fluid levels in tissue can arise as a result of introduction of a fluid into the body, for example, during an injection procedure. In that regard, in many medical diagnostic and therapeutic procedures, a physician or other person injects fluid into a patient's blood vessels. Moreover, in recent years, a number of injector-actuated syringes and powered injectors for pressurized injection of contrast medium in procedures such as angiography, computed tomography, ultrasound and NMR/MRI have been developed.

Extravasation or infiltration is the accidental infusion or leakage of an injection fluid such as a contrast medium or a therapeutic agent into tissue surrounding a blood vessel rather than into the blood vessel itself. Extravasation can be caused, for example, by rupture or dissection of fragile vasculature, valve disease, inappropriate needle placement, or patient movement resulting in the infusing needle being pulled from the intended vessel or causing the needle to be pushed through the wall of the vessel. High injection pressures and/or rates of some modem procedures can increase the risk of extravasation. In computed tomography, for example, contrast injection flow rates can be in the range of 0.1 to 10 ml/s.

Extravasation can cause serious injury to patients. In that regard, certain injection fluids such as contrast media or chemotherapy drugs can be toxic to tissue. It is, therefore, very important when performing fluid injections to detect extravasation as soon as possible and discontinue the injection upon detection.

Several extravasation detection techniques are known in the art. Two simple and very useful techniques for detecting extravasation are palpation of the patient in the vicinity of the injection site and simple visual observation of the vicinity of the injection site by a trained health care provider. In the palpation technique, the health care provider manually senses swelling of tissue near the injection site resulting from extravasation. By visual observation, it is also sometimes possible to observe directly any swelling of the skin in the vicinity of an injection site resulting from extravasation.

In addition to palpation and observation, there are a number of automated methods of detecting extravasation that may include automatic triggering of an alarm condition upon detection. Unfortunately, each of these automated methods of detecting extravasation is limited by significant drawbacks.

In that regard, several plethysmographic detection techniques are available. For example, mercury strain gauge plethysmographs measure the volume change resulting from venous blood flow in a cross sectional area of a limb of a patient. Air cuff or pulse volume recorder plethysmographs measure the changes in pressure within a recording cuff. Such plethysmographs can be cumbersome to operate and/or insensitive to small changes in volume.

Impedance plethysmographs use low-frequency electromagnetic energy transmitted via galvanic contact with the skin to measure changes in the electrical impedance in a defined tissue volume of a limb. Detection of extravasation via impedance changes is disclosed, for example, in U.S. Pat. Nos. 5,964,703 and 5,947,910. In this method, an impedance change of a certain level relative to a baseline measurement in the vicinity of the injection site is interpreted as being an extravasation. A change in impedance occurs during extravasation because injection fluid in the tissue of the patient changes both the volume and the electrical impedance properties of the tissue. Use of electrodes in impedance plethysmographs can, however, result in instabilities. For example, maintaining suitable electrical (ohmic or galvanic) contact between the electrodes of impedance plethysmographs and the skin of the patient is often very difficult.

Photo-plethysmographs measure the optical scattering properties of capillary blood to detect the presence of extravasated fluids in tissue. An example of a photo-plethysmograph is described in U.S. Pat. No. 4,877,034. Because light is heavily absorbed in tissue, however, the sensitivity of photo-plethysmographs is generally limited to the top ¼ inch of tissue. Many extravasations, however, occur deeper than ¼ inch. Moreover, the injection medium may flow into interstitial spaces remote from the photoplethysmograph sensors and go undetected.

A number of extravasation detection devices attempt to measure temperature differences to determine if an extravasation has occurred. For example, U.S. Pat. No. 4,647,281 discloses subcutaneous temperature sensing of extravasation to trigger an alarm. In this method of extravasation detection, an antenna and a microwave radiometer instantaneously measure the temperature of the subcutaneous tissue at the site where fluid is injected by measuring microwave radiation emitted naturally from the body. An algorithm periodically determines the temperature difference between tissue and injected fluid, and compares the difference to a fixed threshold. An alarm processor uses the comparison to determine an alarm condition.

In addition, U.S. Pat. No. 5,334,141 discloses a microwave extravasation detection system employing a reusable microwave antenna and a disposable attachment element for releasably securing the microwave antenna to a patient's skin over an injection site. The attachment element holds the antenna in intimate contact with the patient's skin to optimize microwave transfer therebetween, while shielding the antenna from environmental noise signals. U.S. Pat. No. 5,954,668 also discloses use of a microwave antenna to sense temperature of tissue to detect extravasation. Although measurement of temperature changes and emissivity using microwave energy can result in instantaneous detection, temperature differences are often too small for practical measurement.

In addition to microwave radiometry for the detection of extravasation as described above, radiometry has also been proposed for the detection of pulmonary edema as described in U.S. Pat. No. 4,488,559. U.S. Pat. No. 4,240,445 discloses detection of pulmonary edema via transmitting electromagnetic energy through a transmission line coupled to tissue. U.S. Pat. No. 4,690,149 discloses detection of brain edema via impedance changes detected by a sensor. A proposed method of detection of brain edema is also disclosed in U.S. Pat. No. 6,233,479, in which a measured signal from a microwave antenna is compared to a stored characteristic edema signal.

Microwave energy has also been used for the detection of tumors in living tissue as described in U.S. Pat. No. 6,061,589. Unlike the passive measurements in microwave radiometry, U.S. Pat. No. 6,061,589 disclosed transmission of electromagnetic energy into the body (breast tissue) using a microwave antenna in and a resultant signal is measured. In that regard, U.S. Pat. No. 6,061,589 describes a microwave antenna to detect incipient tumors in accordance with differences in relative dielectric characteristics. Electromagnetic energy in the microwave frequency range is applied to a discrete volume in the tissue and scattered signal returns are collected. The irradiated location is shifted or changed in a predetermined scanning pattern. The returned signals are processed to detect anomalies indicative of the present of a tumor.

Magnetic resonance has been proposed for use in water content mapping in human tissue as described in U.S. Pat. No. 5,995,863. Microwave energy has also been used as in non-invasive tomographic spectroscopy imaging. See U.S. Pat. Nos. 6,332,087 and 6,026,173.

Microwave energy has further been used to measure the fat content in nonliving organic tissue. For example, M. Kent, "Hand Held Fat/Water Determination in whole Fish", Food Control, 1:47–53 (1990), discloses a microstrip sensor for such a determination. In general, the fat content of pelagic and other fatty species of fish is proportion to water content. The dielectric properties of the fish depend on the water content. In the device of Kent, changes in transmission properties of the fish were calibrated against water content.

It is very desirable to develop improved devices and methods for detecting elevated or otherwise abnormal levels of fluids in living tissue (for example, as a result of edema, hematoma or extravasation).

SUMMARY OF THE INVENTION

In one aspect, the present invention provides method of detecting a change (that is, an increase or a decrease) in the level of fluid in tissue in a first area of a body including the steps of: applying electromagnetic energy in the frequency range of approximately 300 MHz to approximately 30 GHz to a first volume of the body; measuring a resultant or returned signal; comparing the signal to a reference signal to determine if the fluid level in the tissue has changed. Preferably, the electromagnetic energy is in the frequency range of approximately 1 GHz to approximately 10 GHz. More preferably, the electromagnetic energy is in the frequency range of approximately 3 GHz to approximately 5 GHz. As used herein, the phrase "comparing the signal to a reference signal" includes comparison of the raw signals as well as comparing functions (including mathematically altered forms) of such signals.

In one embodiment, the method of the present invention detects changes in the level of fluid in tissue of a body by applying electromagnetic energy to a first volume of the body over a period of time (for example, using an antenna or antennae); measuring a resultant signal or a signal returned from the tissue; and comparing the signal to a reference signal to determine if a level of fluid in the tissue has changed during the period of time.

In the case that one is monitoring for a changed fluid level (for example, an elevated fluid level) resulting from extravasation of an injected fluid, the method further includes the step of injecting an injection fluid into the body, typically in the vicinity of the tissue being monitored. In addition to the detection of changing fluid levels in tissue as a result of "foreign" or introduced fluids (regardless of the manner of introduction), the present invention is equally suited for the detection of changed levels (for example, elevated levels) of natural body fluids as can occur, for example, in the case of edema, hematoma, ruptured bowel or colostomy tubing leakage into the peritoneal cavity.

In many cases, the fluids detected in the methods of the present invention are interstitial fluids in that the changing, elevated or abnormal fluid levels detected in the present invention arise from the presence of fluids outside and/or between organized structure (for example, cells, veins, muscle, fat etc.) within the body.

The reference signal can, for example, be a baseline signal measured in the first volume of the body. For example, a signal measurement can be made before an injection procedure or at the inception of an injection procedure before any extravasation of an injection fluid has occurred. The baselines used in the present invention can be the result of a single measurement made at one point in time or the baseline can be a "running baseline," For example, a signal measurement resulting from application of electromagnetic energy to the first volume can be compared to one or more other signal measurements or a mathematical function (for example an average) of one or more other signal measurements resulting from application of electromagnetic energy to the first volume a predetermined amount of time earlier. If the signals differ by a predetermined amount or in a predetermined manner, a positive determination/alarm can be provided. In this manner, shifts or drifts in a baseline measurement over time resulting, for example, from patient movement or changes in volume/flow rate of injected fluids can be prevented from causing false positive or false negative determinations. In other words, a slow rate in change in the measured signal would not be interpreted as positive determination of a change in fluid level in the tissue whereas a rapid rate of change in the measured signal would be interpreted to correspond to a change in fluid level in the tissue.

The reference signal can also be produced by applying electromagnetic energy (for example, in the frequency range of approximately 300 MHz to approximately 30 GHz) to tissue in a second volume of the body in which the fluid level is known or normal (that is, not changed, elevated or otherwise abnormal). Preferably, the tissue in the second volume is similar in electrical properties to the tissue in the first area. The reference signal can also be developed by applying electromagnetic energy (for example, in the frequency range of approximately 300 MHz to approximately 30 GHz) to a volume of tissue of a plurality of bodies to develop an aggregate reference. The tissue of each of the plurality of bodies preferably does not have an elevated or otherwise abnormal level of fluid therein when the reference measurement is made.

In general, the measured signal in the method of the present invention is altered by changes in the bulk value or specific makeup of the dielectric properties (that is, complex electrical permittivity and/or magnetic permeability) of the region of interest in the tissue. Such changes can, for example, be caused by changes in overall fluid level(s) in the region of interest. For example, in the case of an extravasation, the injection fluid can invade the region or volume of tissue being monitored. Some extravasated fluids (for example, certain chemotherapy drugs) can invoke a response by the body including an increase in the level of body fluids that can invade the region or volume being monitored. The dielectric properties of tissue can change measurably in the case that fluid levels become elevated within the tissue, in many cases because of the presence of water in an introduced fluid or fluid from the body which has dielectric properties differing from normally hydrated tissue. Moreover, changes is the level of fluid in volumes or regions in the vicinity of the volume or region being monitored can also be detected even though the level of fluid in the region or volume being monitored has not changed. In that regard, sub-regions of fluid that are introduced or removed can cause movement of boundaries where differing dielectric properties meet in the region or volume being monitored and change the path and nature of the received signal.

The step of applying electromagnetic energy can include the step of placing a transmitter in the vicinity a body surface (for example, skin or an internal body organ). The transmitter preferably includes an antenna (for example, a resonant structure) that transmits energy such as a microwave antenna. The antenna of the transmitter need not be in direct contact with the skin or other surface. For example, the transmitter can include at least one layer of material contacting the skin or other surface that, for example, separates the transmitter from the skin or other surface and electrically couples with the skin or other surface by having a similar, intermediate, or intentionally chosen intrinsic impedance (resistance to microwave propagation), but not necessarily the same complex dielectric properties, to the skin or other surface of interest.

In still another aspect, the present invention provides a method of detecting changes in the level of fluid in tissue of a body including the steps of: transmitting electromagnetic energy using an antenna (or antennae) in the vicinity of a surface of the body such that changes in the surface geometry of the surface resulting from a change in fluid level of underlying tissue affect a resultant signal; measuring the resultant signal; and comparing the resultant signal to a reference signal. For example, a electromagnetic energy can be transmitted across the surface (for example, across skin or across a surface internal to the body such as the surface of an organ) from a transmitter to a receiver. Alternatively, electromagnetic energy can be transmitted to a surface and signals reflected therefrom measured.

In another aspect, the present invention provides a method of detecting extravasation of a fluid injected into a vascular structure of a body in tissue outside of the vascular structure, including the steps of: applying electromagnetic energy in the frequency range of approximately 300 MHz to approximately 30 GHz a first volume of the body during a period of time in which a fluid is injected into the vascular structure; measuring a resultant signal; and comparing the signal to a reference signal to determine if fluid level in the tissue has changed during the period of time.

In another aspect, the present invention provides a method of detecting extravasation including the steps of: placing an antenna (or antennae) in operative connection with the skin of the body; applying electromagnetic energy to a first volume of the body using the antenna; injecting the fluid into a vascular structure of the body (typically, in the vicinity of the tissue); measuring a returned signal; and comparing the signal to a reference signal to determine if extravasation has occurred.

In a further aspect, the present invention provides a device for detecting changes in fluid levels in tissue of a body including at least a first transmitter to transmit electromagnetic energy to a first volume of the body. The device also includes at least a first receiver to measure a returned signal and a memory storing a reference signal. The reference signal is created by transmitting electromagnetic energy into the first volume of the body and measuring a resultant signal (typically, earlier in time than the returned signal). The device also includes a signal processor in communication with the first receiver and the memory. The signal processor compares the returned signal to the reference signal to determine if the level of fluid in the tissue of the body has changed.

In another aspect, the present invention provides an injection system including an injector to inject a fluid into a vascular structure in a body. The injection system also includes at least a first transmitter including an antenna to transmit electromagnetic energy to a first volume of the body and at least a first receiver to measure a returned signal. A memory of the injection system stores a reference signal or signals, which are created by transmitting electromagnetic energy into the first volume of the body prior to an injection and measuring a resultant signal. The injection system further includes a signal processor in communication with the first receiver and the memory. The processor compares the returned signal(s) to the reference signal(s) to determine if the level of fluid in tissue outside the vascular structure has changed.

In another aspect, the present invention provides a system for injection of an injection fluid into a body including a pressurizing chamber (in which injection fluid is pressurized for injection into a vascular structure of a body) and an extravasation detector. The extravasation detector includes at least a first transmitter including an antenna to transmit electromagnetic energy to a first volume of the body. The extravasation detector further includes at least a first receiver to measure a returned signal. A memory stores a reference signal or signals, which are created by transmitting electromagnetic energy into the first volume of the body prior to an injection of fluid and measuring a resultant signal. The extravasation detector further includes a signal processor in communication with the first receiver and the memory. The processor compares the returned signal(s) to the reference signal(s) to determine if the level of fluid in tissue outside the vascular structure has changed.

In still a further aspect, the present invention provides a method of detecting a change in the level of fluid in tissue of a body including the steps of: applying electromagnetic energy to a first volume of the body using at least one antenna; measuring a resultant signal using at least one other antenna; and comparing the signal to a reference signal.

In many instances, the changes in fluid levels in living tissue measured by the methods of the present invention are relatively "dynamic" changes. As used herein, the term "dynamic" refers generally to a change that occurs during a relatively short time frame. In the case of edema, hematoma and extravasation this period of time can, for example, be in the range of one or more seconds to several days (for example, three days).

In the case of extravasation, the present invention easily affords the ability to detect extravasation at the injection site and/or any position or site remote from an injection site, for example, along a path of potential extravasation. In that regard, extravasation sometimes occurs at a site remote from the catheter insertion point (that is, the injection site). Multiple energy sources and/or multiple sensors may be positioned along a path of potential extravasation.

Numerous other advantages are afforded by the apparatuses, systems and methods of the present invention as compared to current apparatuses, systems and methods of detecting extravasation and other abnormal fluid levels in the body. For example, a larger portion of tissue can be probed for the presence of elevated or otherwise abnormal fluid levels. Likewise, the sensors, systems and methods of the present invention can be mobile with the patient to, for example, measure for development of hematoma after a head injury patient leaves a hospital. Moreover, the use of, for example, microstrip antennae in the present invention provides sensors of relatively low profile that are unobtrusive to both the patient and medical personnel.

Unlike prior modalities, detection of extravasation in the present invention is not sensitive only in superficial layers of tissue, but can preferably reach through the entire tissue volume into which injection fluid can migrate in the case of extravasation.

Moreover, the detection site(s) (for example, an injection site) can remain open for visualization and/or palpation. Likewise, tight coupling of transducers to the patient's skin and attendant discomfort and/or tissue damage are avoided.

The present invention and its attendant advantages will be further understood by reference to the following detailed description and the accompanying drawings.

BRIEF DESCRIPTION OF THE DRAWINGS

FIG. 1 illustrates one embodiment of a detection system of the present invention.

FIG. 2 illustrates the detection system of FIG. 1 in use to detect extravasation.

FIG. 4B illustrates a side view of use of an antenna array as illustrated in FIG. 4A to pass electromagnetic energy across a surface to detect a change in, for example, the geometry, shape or morphology of the surface corresponding to a change in fluid level in underlying tissue.

FIG. 4C illustrates a side view of an antenna used to transmit electromagnetic energy to and measure reflected electromagnetic energy from a surface to detect a change in, for example, the geometry, shape or morphology of the surface corresponding to a change in fluid level in underlying tissue.

FIG. 19A illustrates complex distance as a function of injected volume and frequency in the upper graph and maximum complex distance over all frequencies as a function of injected volume in a lower graph for an extravasation study on a double-skinned chicken phantom.

FIG. 19B illustrates complex distance as a function of injected volume and frequency in the upper graph and maximum complex distance over all frequencies as a function of injected volume in a lower graph for another extravasation study on a double-skinned chicken phantom.

FIG. 19C illustrates complex distance as a function of injected volume and frequency in the upper graph and maximum complex distance over all frequencies as a function of injected volume in a lower graph for an extravasation study on a single-skinned chicken phantom.

DETAILED DESCRIPTION OF THE INVENTION

Figure 3:
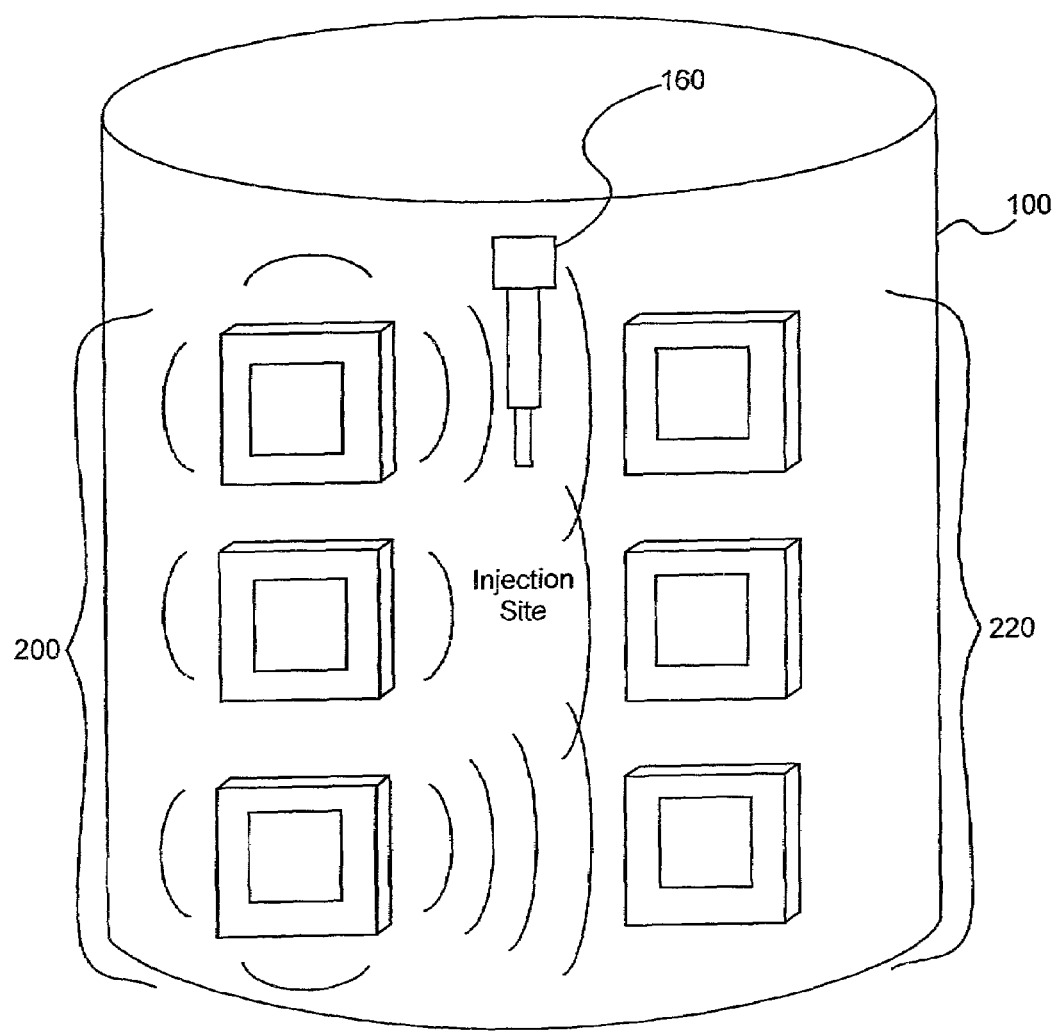
FIG. 3 illustrates an embodiment of an antenna array of the present invention positioned about an injection site in the detection of extravasation.

While the sensors, systems and methods of the present invention are generally applicable to the sensing any fluid within body tissue (whether a body fluid or an introduced fluid), the present invention is primarily described herein with reference to the representative example of extravasation of a fluid intended to be injected into a vascular structure. However, one skilled in the art appreciated that elevated, abnormal or changing levels of generally any fluid can be detected using the sensors, systems and methods of the present invention. Detection of body fluids in the present invention includes, but is not limited to, the detection of fluid changes as a result of edema, hematoma, ruptured bowel and colostomy tubing leakage into the peritoneal cavity. Introduced or foreign fluid detectible in the present invention include fluid introduced via generally any technique known in the medical arts including, but not limited to, injection, infusion and IV drip. As described above, changes in complex permittivity and permeability as a result of changing fluid levels in tissue are detected by application of electromagnetic energy to the tissue and detection of a resultant signal.

Complex permittivity and permeability govern how an electromagnetic wave will propagate through a substance. Complex permittivity typically has the greatest effect since it varies significantly between tissue types and fluids of interest. The complex permeability of various tissues and many fluids of interest is approximately that of a vacuum, reducing the effect of this parameter. However, some fluids such as MRI contrast agents may have an appreciable complex permeability difference from tissue. Although blood contains small amounts of iron, the permeability value for any significant volume of blood is typically insignificant. Complex permittivity is generally expressed as $$\epsilon^* = \epsilon' - j\epsilon''$$

wherein $\epsilon'$ is the real component of the complex value and is known as the dielectric constant or sometimes simply referred to as the "permitivitty." The term $\epsilon''$ is the imaginary component of the complex value and is often referred to as the "loss factor." The ratio of ($\epsilon''/\epsilon'$) is known as the "loss tangent." The complex permittivity (and sometimes permeability) of certain substances differ from the body tissue at certain frequencies. In the present invention, such differences in permittivity and/or permeability are used for the detection and level monitoring of certain fluids and substances in biological tissue.

The studies of the present invention have shown that electromagnetic energy having, for example, a frequency in the range of approximately 300 MHz to approximately 30 GHz (and, more preferably, in the range of approximately 1 GHz to approximately 10 GHz, and, even more preferably, in the range of approximately 3 GHz to approximately 5 GHz) provides good penetration into tissue. In general, such electromagnetic energy is launched into the subcutaneous tissue and a resultant signal is measured. Electromagnetic energy in the frequency range set forth above has been found to transmit through the skin and to transmit or propagate well within, for example, fat. Good transmission through the fat layer is beneficial for detection of extravasation as many extravasations occur in the fat layer. The sensitivity to extravasation of the systems, devices and methods of the present invention is thus increased as compared, for example, to impedance plethysmography. In the case of impedance plethysmography, the majority of the electrical current passes through highly conductive layers such as skin and muscle in which extravasation is much less likely to occur.

In one embodiment of the present invention, one or more transmitting antenna(e) can be placed on one side of the tissue to be analyzed or monitored and one or more receiving antenna(e) can be placed on another side of the tissue. Using this configuration, the presence or level of a foreign material, liquid, body fluid, or substance in the subcutaneous tissue can be determined. As illustrated in FIG. 1, one or more electromagnetic sources 10 (typically antennae, including, for example, resonant structures,) transmit an electromagnetic wave into the tissue in an area of interest (for example, a portion of an arm 100 of a human patient). The scattered and/or reflected wave is then received by the launching antenna(e) (represented by the dashed line in FIG. 1) and/or by one or more receiving antenna(e) 20. A signal can be transmitted and received with a single antenna using, for example, directional couplers as known in the art whereby the active antenna(e) become not only the source but the sensing element. Using multiple receiving antennae can be advantageous as noise, motion artifact, or other anomalies can sometimes be more readily discerned from changes caused by changes in presence or level of fluid/substance of interest.

A signal is supplied to active antenna(e) 10 from one or more signal sources 30. Signal source(s) 30 is preferably in communicative control with a data processing and control unit 40 (for example, a computer). Control unit 40 can be in communication with user interface 50 (for example, a keyboard, a monitor etc.) and an alarm 60. Data processing and control unit 40 is also preferably in communication with a signal processor 70 which receives signals from antenna 10 and/or antenna 20.

In general, the present invention is well suited for the detection of abnormal and/or changing levels of a variety of fluids in the human body, including both body fluid and foreign substances as described above. In several embodiments of the present invention, one or more antennae (for example, resonant structures) as described above can be used to determine if an extravasation has occurred during an injection procedure. Several antenna(e) designs, configurations and/or placements are described below in the context of detection or determination of extravasation.

For example, FIG. 2 illustrates the use of the detection system of FIG. 1 in the detection of an extravasation 120 during an injection procedure. Transmitting antenna 10 and receiving antenna 20 are positioned on opposing sides of an injection site wherein a catheter 160 is positioned within, for example, a vein 110. Catheter 160 can, for example, be in operative connection with a source of pressurized injection fluid such as a syringe 170 in connection with a powered injector 180 as known in the art.

The present invention uses electromagnetic waves in the RF and microwave region, well below the optical frequency range. Applicators/antennae to transmit and/or receive electromagnetic energy for use in the present invention are, for example, resonant structures and may take on several forms including, but not limited to, the following: microstrip antenna(e), waveguide(s), horn(s); helical antenna(e) and dipole antenna(e) as known in the art. As used herein, the term "microstrip antenna" refers generally to a thin, low-profile antenna of a wide variety of patterns including, but not limited to, linear, square, circular, annular ring, triangular, rectangular, dipole, tapered slot and others.

In the RF and microwave frequency electromagnetic energy ranges of the present invention, resonant structures or other energy transmitting antennae interact with the tissue of interest via nearfield interactions and propagated waves. Energy is exchanged with the tissue in the nearfield and waves are propagated into the tissue. Reflections and scattering occurs at boundaries when permittivity and/or permeability variations and differences occur.

In the present invention, a measured signal is compared to a reference signal or signals to determine if an abnormal (for example, elevated) level of fluid is present in the area of tissue being monitored. A reference signal can, for example, be a baseline signal that is measured when the fluid/substance level of interest is known or in a known state. Following the baseline, a search mode is entered where changes in a reflected or scattered waves are detected by measuring the received signal(s) and comparing them to the reference signal(s). If, for example, the measured signal deviates from the reference signal by a predetermined amount or in a predetermined manner, alarm 60 can be activated. In an injection procedure, the injection can be stopped upon activation of alarm 60. For example, control unit 40 can be in communication with powered injector 180 to stop an injection procedure upon detection of extravasation.

Measurements and signal processing can, for example, be made in the time domain and/or the frequency domain as known in the art. In the frequency domain the signal source is generally a sinusoidal wave source in which the frequency is swept or stepped. At each frequency of interest, the magnitude and/or phase of the measured signal can be compared to the magnitude and/or phase of the reference signal to detect changes of, for example, a pre-determined amount. Alternatively, in the time domain, the signal source can be a substantially narrow impulse or sharp step that excites the resonant modes of the sending antenna(e) which in turn launches an electromagnetic wave into the tissue of interest. Fluid or substance presence or level changes alter the received signal(s) such that they differ from the reference signal in terms of delay, frequency content, and/or overall shape.

The present invention also embodies other types of measurements and signal processing. When using the same antenna(e) to send and receive energy, such measurement modes can include, for example, antenna impedance or resonant mode frequency shift detection. Furthermore, more sophisticated signal processing techniques of the reference and/or received signals can be employed. For example, the signals may be mathematically manipulated, such as averaged, integrated, median filtered, band pass filtered, low pass filtered, or high pass filtered in the time or frequency domain to emphasize subtle patterns in the data that may not be as readily apparent when simple reference subtraction/comparison is performed.

In general, to compare or to make a comparison refers to making a decision or judgment based upon a relationship between two or more measurements, sets of measurements, or functions of measurements. The relationship is generally expressed as a mathematical relationship, algorithm, or heuristic. For example, a comparison of magnitude or complex distance from a baseline measurement (as further described below) can be made. It is also possible to compare the slopes or rate of change of the received and reference signals. An algorithm similar to that applied in statistical process control can, for example, be applied whereby an abnormality is judged to occur if more than a predetermined number of successive measurements (for example, four successive measurements) are on one side of the reference signal, or if one measurement is outside of a standard band, or if there is a trend of a predetermined number of measurements (for example, seven measurements) moving in a consistent direction. As known to those skilled in the art there, are many other comparisons that can be made.

In one configuration of the present invention as illustrated in FIG. 3, two generally linear arrays of antennae are used. In one embodiment of this configuration, one array of antennae is an active (launching/transmitting) array 200 and an opposing array of antennae on the other side of the injection site is the passive (receiving) array 220. The signal source of the system excites or drives active array 200 via, for example, amplifiers by using sinusoidal or impulse waveforms. The signal source(s) create an electromagnetic wave which is launched generally normally (perpendicularly) to the skin surface and into the subcutaneous tissue. The wave then scatters and propagates through the subcutaneous tissue (for example, through adipose/fat tissue). Tissue layers that are more conductive than fat, such as muscle and skin, tend to reflect and guide the electromagnetic energy. The antennae of passive antennae array 220 then receive the signals which are, in turn, processed by the signal and data processing subsystems. The received or measured signals are then compared to the reference (for example, baseline) signals that were collected during the baseline procedure. As discussed above, baseline measurements can be repeated or updated to create a running baseline. As known by those skilled in the art, a wide variety of microstrip antenna designs are suitable for use in the present invention including: line, square, circular, annular ring, triangular, rectangular, dipole, tapered slot and others. In general, any design that yields sufficient energy coupling in the preferred frequency ranges set forth above are suitable for use in the present invention.

Figure 4A:
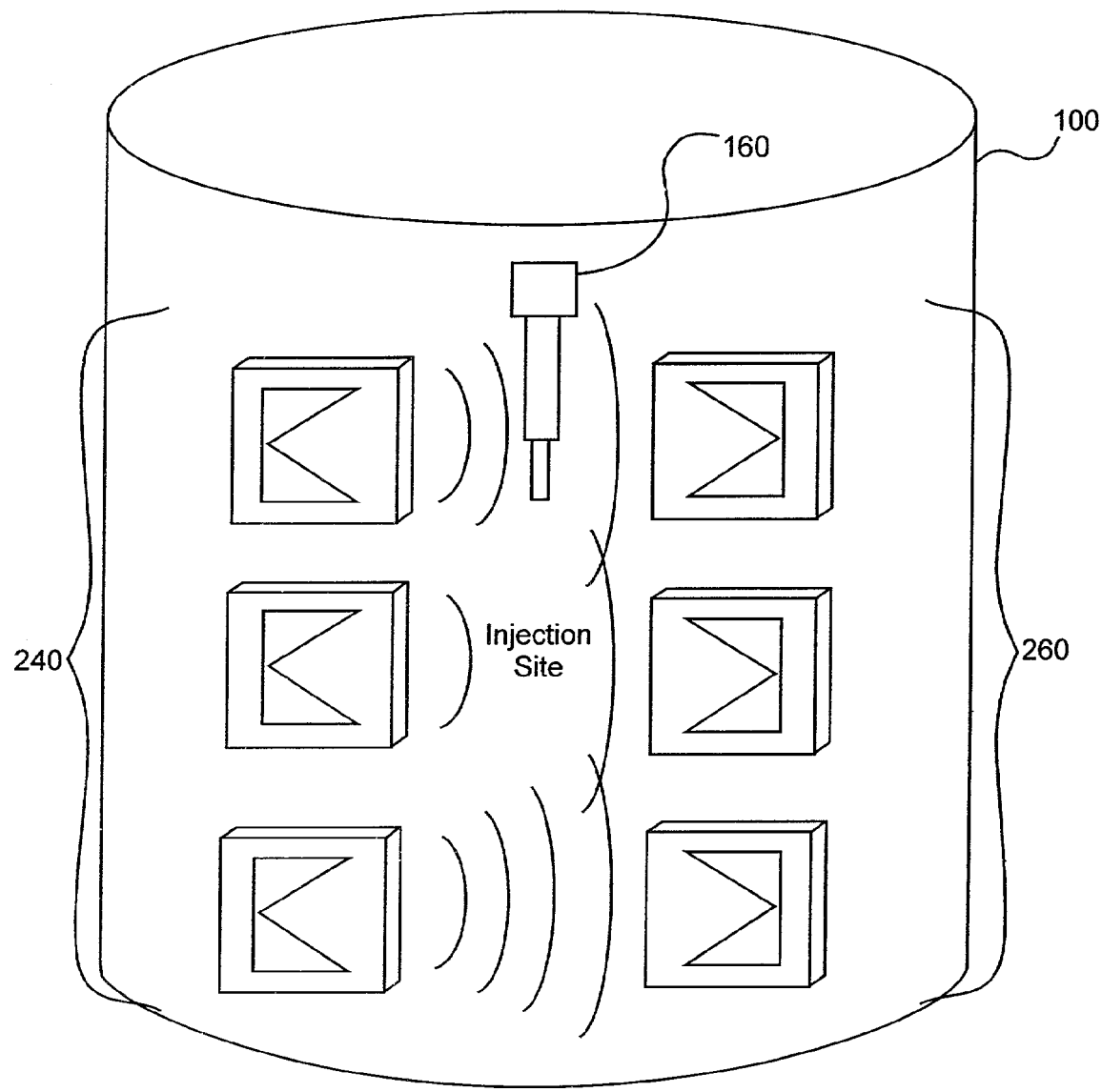
FIG. 4A illustrates another embodiment of an antenna array of the present invention including tapered-slot antennae.

In FIG. 4A, a generally linear array 240 of transmitting microstrip antennas with a tapered-slot design are illustrated. The tapered-slot design yields improved directionality and increased bandwidth. The antennae or array 240 can be angled toward the skin of arm 100 so that the waves can be launched into the tissue, yet in the general direction toward passive/receiving antennae 260. Use of such tapered-slot is antennae can improve signal coupling and overall sensitivity.

In another embodiment of the present invention, electromagnetic waves are propagated in the vicinity of the surface of the skin or other body surface using antennae (for example, arrays of antennae as illustrated in FIG. 4A) above or close to the surface. The propagated waves interact with the surface in a manner that is affected by the surface shape, geometry or morphology. This method can be useful, for example, when the tissue of interest has a thin fat layer. In this embodiment of the present invention, surface/skin deformation caused by the fluid/substance of interest can be detected by monitoring signals reflected and/or scattered by the surface. Tapered-slot antennae in a configuration similar to that shown in FIG. 4A can, for example, be used to propagate surface waves across moderately conductive skin. For example, FIG. 4B illustrates transmission of electromagnetic waves across the surface of arm 100 by a pair of transmitting/receiving antennae 250a and 250b. Surface deformation caused by changed, elevated or abnormal fluid levels (for example, extravasation) induce a change in the signal measured by antenna(e) 250a and 250b. FIG. 4C illustrates another embodiment in which a transmitting/receiving antenna 260 transmits electromagnetic energy generally normal to the surface of arm 100 and receives a reflected signal. Once again, surface deformation induces a change in the measured signal. In the embodiment of FIG. 4C, separate transmitting and receiving antennas can be used as described above as either a single antenna pair or as an array of multiple transmitting/receiving antennas.

Figure 5:
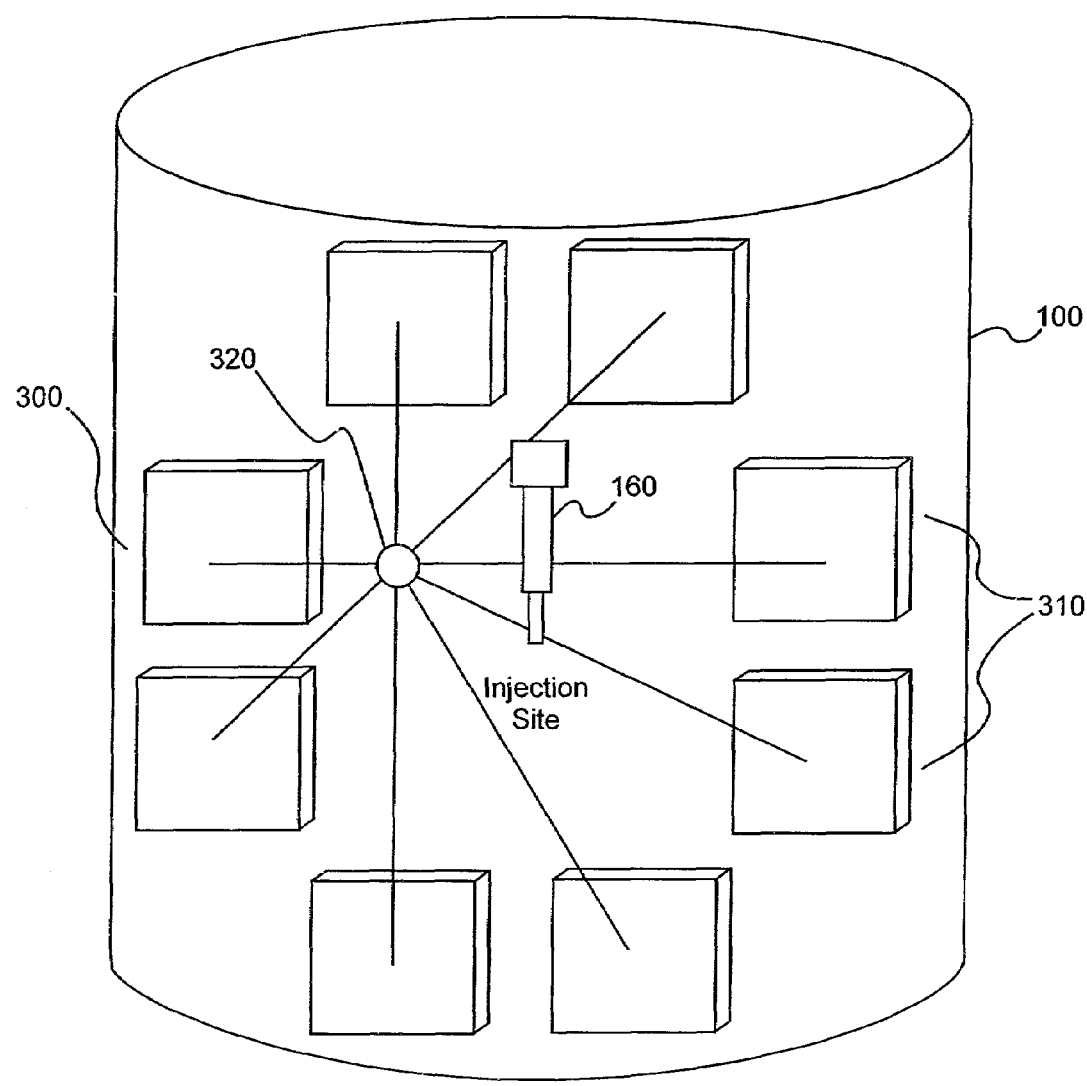
FIG. 5 illustrates another embodiment of an antenna array of the present invention.

Another embodiment of an antenna array or configuration 300 is shown in FIG. 5 wherein a plurality of antennae 310 are arranged to surround the area to be monitored. The web array of antennae 310 in FIG. 5 enables a phasing approach to concentrate the wave energy at a particular location 320. The phased drive signals to each antenna can then be altered such that the focal point 320 is moved in a scanning pattern. This phasing approach can increase the overall sensitivity of the system. Furthermore, directional couplers can be employed as known in the art to allow the transmitting antennae in the web array to also perform as receiving antennae.

The present invention in not limited to the antenna configurations or arrays set forth above. A wide variety of antenna configurations are suitable for use in the present invention. In general, any antenna configuration positioned near the anticipated location of the liquid or substance to be detected or monitored is suitable.

For example, extravasation typically occurs in the immediate vicinity of the injection site, near the position of the catheter tip. Extravasation may sometimes occur, however, at a site remote from the injection site. In the present invention, extravasation can be detected at the injection site and at site(s) remote from an injection site (generally along a path of potential extravasation) using, for example, antennae positioned as an array along a path of potential extravasation.

Figure 6:
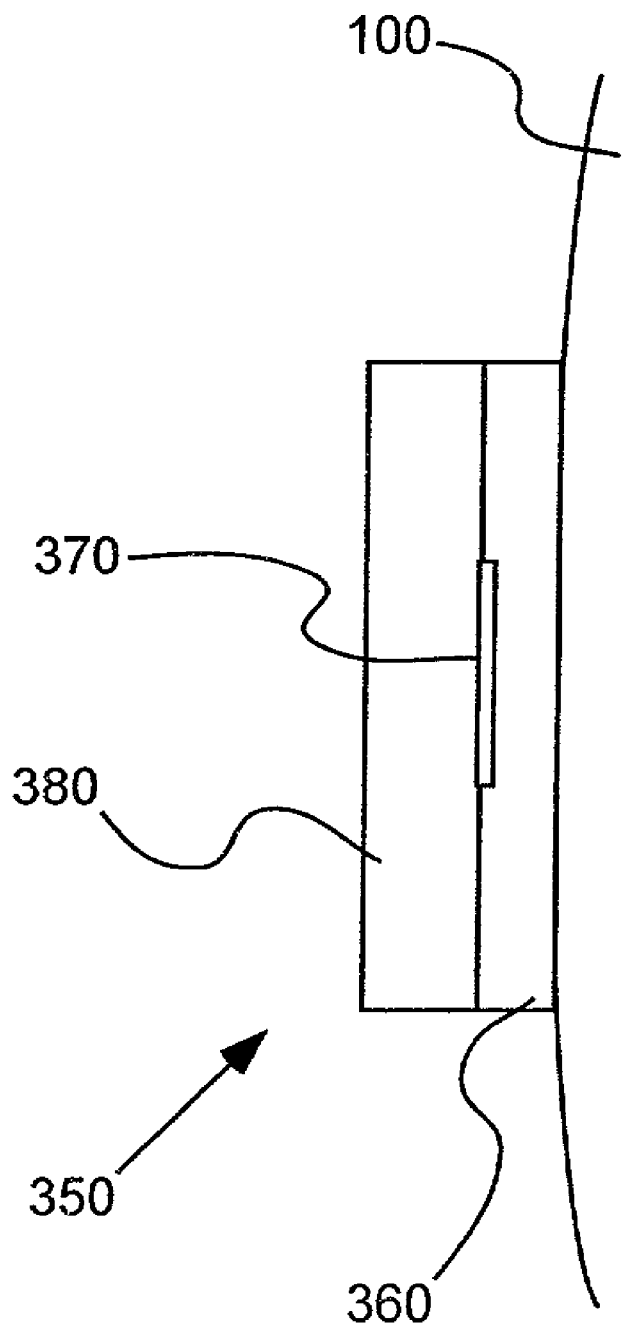
FIG. 6 illustrates an embodiment of a transmitter and/or receiver of the present invention including a coupling or superstrate layer suitable to couple the transmitter/receiver to the skin.

Because certain body surfaces such as skin are somewhat reflective to electromagnetic waves in the frequency ranges used in the present invention, coupling the waves into the surface and tissue can improve system performance. Coupling can, for example, be improved by providing a layer of material in contact with the skin/other surface of interest (for example, the surface of an internal organ) that couples with the surface by having an intrinsic impedance similar to the surface. Such material include, for example, relatively high permittivity low-loss materials such as magnesium calcium titanium-dioxide (Mg—Ca—TiO$_2$). A disposable de-ionized water pouch can also be used. Preferably, deformation of such a water pouch or container during use thereof is limited as deformation can impact the received or measured signal. In that regard, a thin-walled, rigid water container can be used or a pressurized water pouch that limits deformation can be used. FIG. 6 illustrates an embodiment of a microstrip antenna 350 used in several studies of the present invention in operative connection with arm 100. An intermediate, spacing or superstrate layer 360 of a coupling material as described above is in direct contact with the skin of arm 100, while an antenna, for example, a resonant structure 370, is spaced from the skin by intermediate or superstrate layer 360. In the embodiment of FIG. 6, resonant structure 370 is positioned within a substrate 380.

Figure 7A:
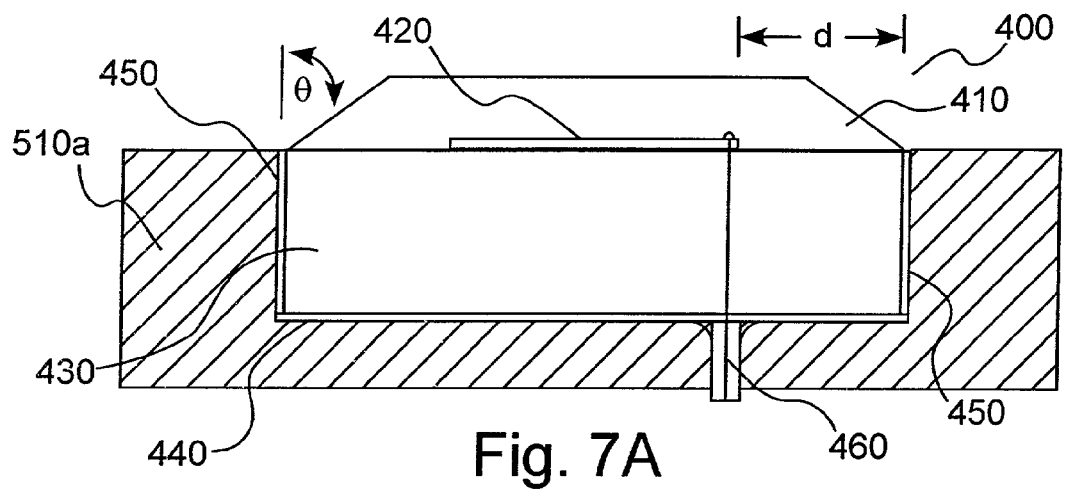
FIG. 7A illustrates a side, cross-sectional view of an embodiment of an antenna of the present invention with a tapered superstrate.
Figure 7B:
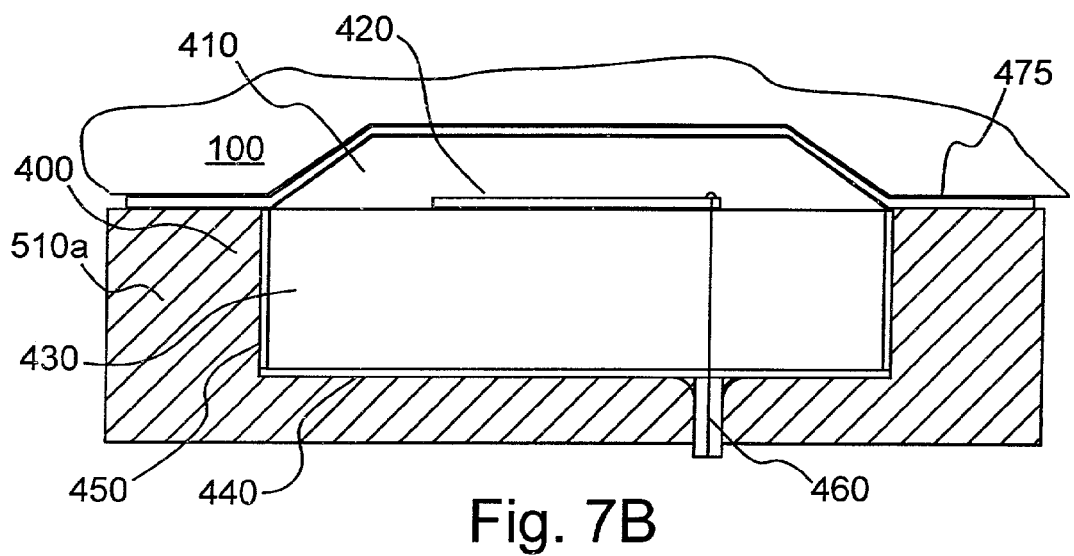
FIG. 7B illustrates a side, cross-sectional view of the antenna of FIG. 7A coupled to a patient's arm.

FIGS. 7A and 7B illustrate another embodiment of a microstrip antenna 400 of the present invention. Like antenna 350, antenna 400 includes a superstrate layer 410 fabricated from a coupling material which contacts the skin of arm 100 (see, for example, FIG. 7B). An antenna or resonant structure 420 is positioned within the confines of a substrate 430. In general, the antennae or resonant structures of the present invention are fabricated from a conductive material such as copper, silver gold or other material as known in the art.

In several embodiments of antennae studied in the present invention, the substrate material was a ceramic material, such as MgCaTiO$_2$. Preferably, the substrate material has a moderate to high dielectric constant (for example, in the range of approximately 10 to approximately 100 and, more preferably, in the range of approximately 50 to approximately 80) or permittivity and low loss. The impedance of the substrate is preferably matched or substantially similar to the impedance of the superstrate, which is, in turn, preferably substantially similar to that of the surface of the tissue to be studied. The material of the superstrate and the substrate can, for example, be the same to prevent discontinuities therebetween, but antennae with differing materials for the superstrate layer and the substrate were fabricated and successfully operated in the studies of the present invention.

The microstrip antennae used in the studies of the present invention were fabricated from a ceramic laminate material coated with thin layers of copper on the front and back thereof. Such a material is, for example, available from Rogers Corporation of Chandler, Arizona under the product name RT/duroid® 6010LM. Such microwave laminates are ceramic-PTFE composites designed for electronic and microwave circuit applications requiring a relatively high dielectric constant. RT/duroid 6010LM laminate has a dielectric constant of approximately 10.2. The laminate was approximately 2.5 mm thick and was supplied with both sides thereof clad with ¼ to 2 oz./ft.$^2$ (8 to 70 μm) electrodeposited copper foil. In fabricating the antennae (or microstrip antennae) of the present invention, some of the copper material was etched from the top of the laminate to form a generally planar antenna element or resonant structure 420, thereby forming a margin between the outer edge of resonant structure 420 and the outer edge of substrate 430. In that regard, a margin d (see FIG. 7A) was created between resonant structure 420 and the periphery of substrate 430. The copper on the bottom side of the laminate formed ground plane 440 of antenna 400. Side shielding 450 of a conductive material can be provided to, for example, improve tissue coupling and prevent stray energy. In certain embodiments, stray surface waves can, for example, increase motion artifact and other artifacts. However, such "stray" or side energy can also be used to monitor surface geometry changes as discussed above in connection with FIGS. 4A through 4C. Silver side shielding was used in several studies of the present invention.

Side shielding 450 and ground plane 440 form an electrically conductive cavity. Preferably, resonant structure 420 and the cavity resonate together in the frequency range of interest. Such resonance matching improves efficiency by, for example, increasing power output relative to power input for transmission, and increasing power received relative to power available for reception. In general, margin size impacts the correspondence, alignment or matching of a patch or resonant structure resonant mode and a cavity resonant mode. It was found by the present inventors that when the diagonal dimension 420d (see FIG. 7D) of a square resonant structure 420 is generally equal to the non-diagonal distance or side width 400w across the cavity (total antenna width), resonant structure 42 and the cavity resonate together in the frequency range of interest. It is believed that the first mode of resonant structure or patch 420 is aligning with the second resonant mode of the cavity. In this embodiment, the matching of the diagonal dimension 420d with non-diagonal distance or side width 400w, determines the size of margin d.

Although square resonant structures 410 were used in the studies of the present invention, it is clear to one skilled in the art that many alternative antenna element or resonant structure geometries (for example, circular or rectangular) can be used in the antennae of the present invention. Circular resonant structures can, for example, provide increase bandwidth as compared to square resonant structures in certain embodiments.

Energy was supplied to resonant structure 420 via, for example, microcoaxial cable 460 as known in the art. In several embodiments, energy was supplied to an inner corner of resonant structure 420 to induce circular polarization. Circular polarization can improve coupling between antennae by decreasing the sensitivity of such coupling to the relative orientations of the antennae. In the fabrication of antennae 400 of the present invention, a base or inner surface of superstrate layer 410 was secured to substrate 430 using an appropriate adhesive, such as a cyanoacrylate or "superglue." In that construction, potential air pockets adjacent resonant structure 420 were filled with the superglue to substantially avoid any negative effect on transmission of the microwaves. However, an indentation corresponding to and receiving the resonant structure 420 can be formed on the underside of superstrate layer 410. Such an indentation can also accommodate a solder bump formed by connection of the center conductor of microcoaxial cable 460.

In several embodiments, the superstrate layer was formed from a ceramic filled PTFE laminate material reinforced with woven fiberglass available from Rogers Corporation of Chandler, Arizona under product number R03210. That material has a dielectric constant of approximately 10.2. It was discovered that beveling the edges of superstrate improved skin conformance and reduce motion artifact in a measure signal resulting from patient movement. As illustrated, for example, in FIG. 7A, the outer edges of superstrate 410 are beveled by an angle θ which is greater than 0° and less than 90°. Preferably, θ is between approximately 20° and 50°. In several of the antennae studied in the Experimental Example set forth below, θ was approximately 30°. In addition to improving skin conformance/coupling, a tapered superstrate can also direct energy toward a receiving antenna in the manner of a microwave lens to improve transmission between antennae. In an alternative to the generally linear taper described above, a curvilinear taper can be used to improve the conformance of superstrate 410 to a patient's skin.

Figure 7C:
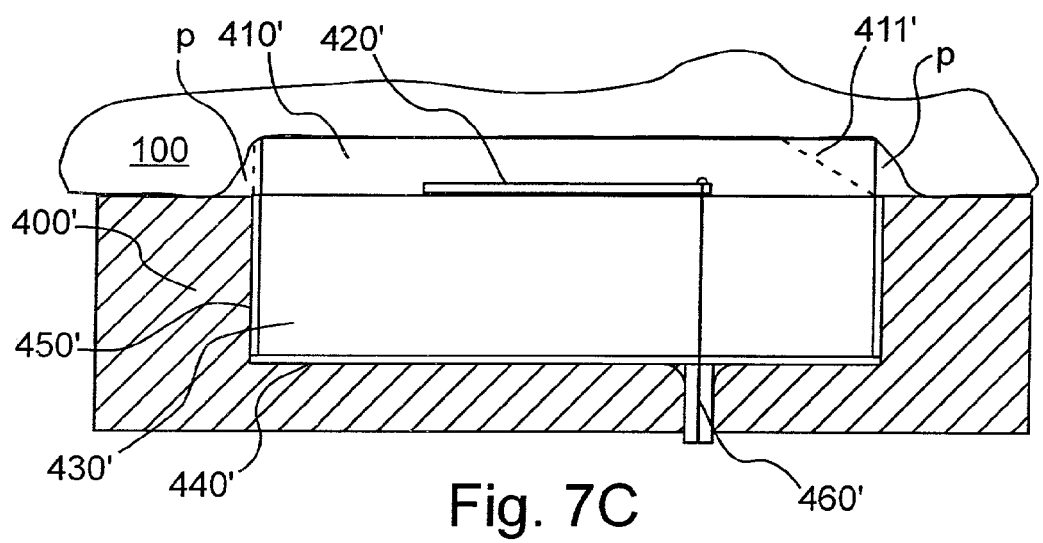
FIG. 7C illustrates a side, cross-sectional view of an antenna of the present invention with a square superstrate coupled to a patient's arm.
Figure 8A:
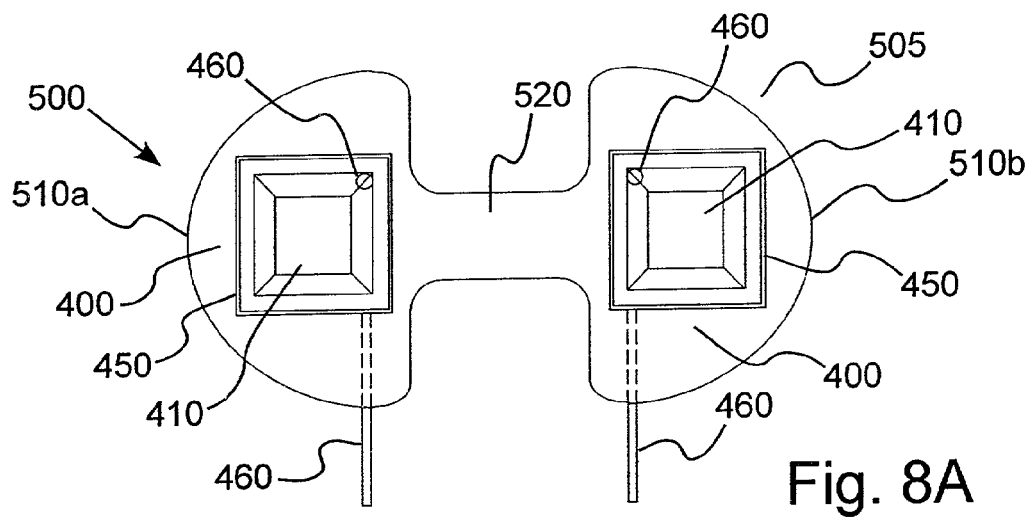
FIG. 8A illustrates a bottom view of a "bowtie" sensor of the present invention including two antenna as illustrated in FIGS. 7A and 7B.
Figure 8B:
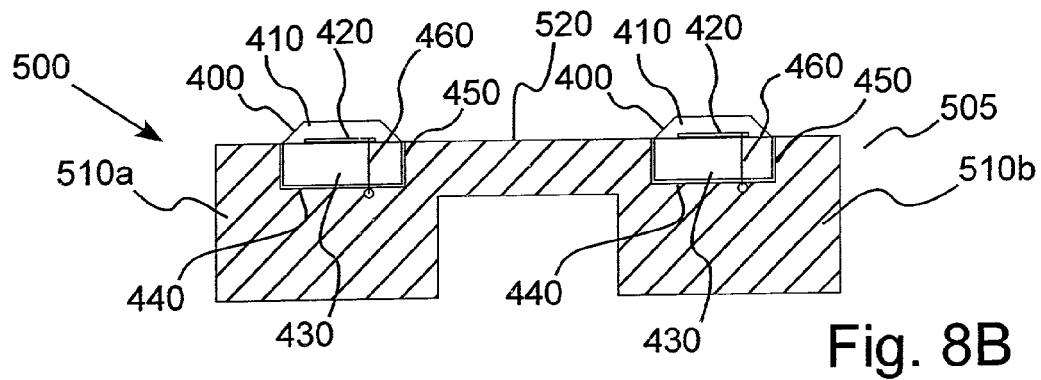
FIG. 8B illustrates a side, cross-sectional view of the sensor of FIG. 8A.
Figure 8C:
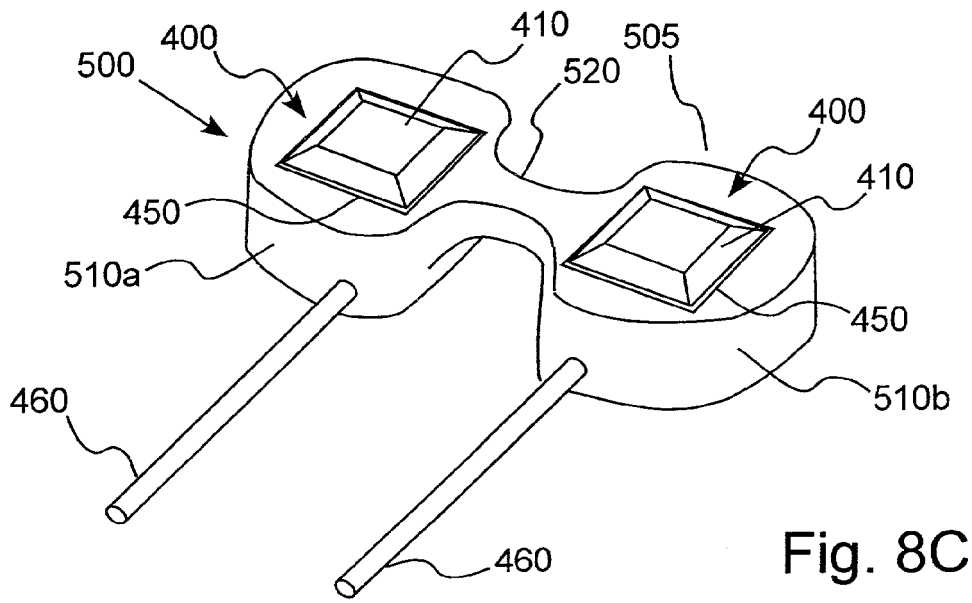
FIG. 8C illustrates a perspective view of the sensor of FIG. 8A.
Figure 7D:
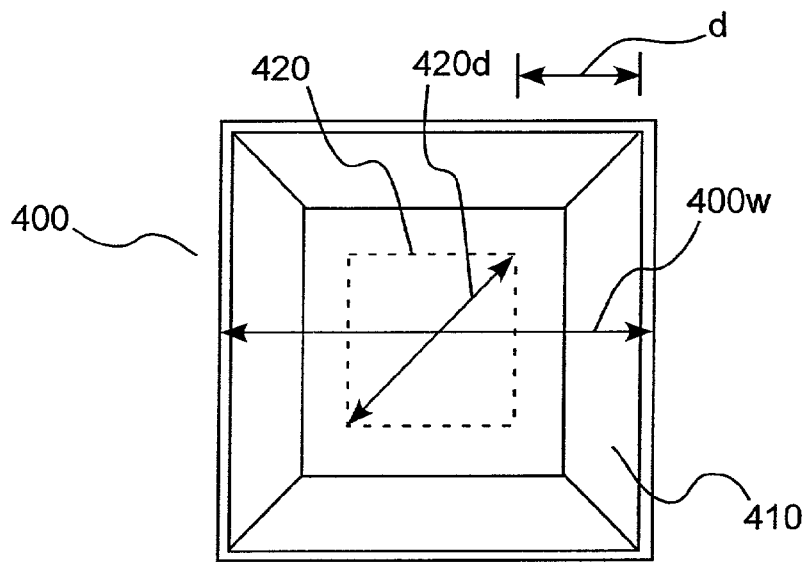
FIG. 7D is a plan view of the antenna of FIG. 7A showing resonance sizing of a square patch antenna element or resonant structure.

FIG. 7C illustrates and antenna 400' which is substantially identical to antenna 400 except that superstrate 410' of antenna 400' is square, rather than beveled. In comparing FIGS. 7B and 7C, it is seen that the skin tissue of arm 100 does not conform as well to the contour of antenna 400' as to the contour of antenna 400, resulting in the formation of air pockets p on the periphery of antenna 400'. Such air pockets can, for example, scatter energy, negatively affect coupling and cause increased artifacts as a result of subject/patient motion.

Antennae of the present invention can be made to have somewhat directional transmission and/or reception of microwaves by having only a portion of the transitional periphery of the outer surface of the superstrate have a generally smooth transition from the base of the superstrate to an outer surface plateau of the superstrate in the desired directional transmission and/or reception. For example, antenna 400' as shown in FIG. 7C can be made to be provide directional transmission and/or receipt of microwaves by making only a portion, such as one side of transitional periphery 411', have a generally smooth transition so that transmission and/or reception is improved in that direction, to the right side of FIG. 7C. For such antenna construction, the shield 450' can be extended as shown by the dotted line. Thus, one or more pairs of antennae can be mated to favor transmission by one antenna and receipt by its mate.

As discussed above, whether the sensors of the present invention comprise a single antenna, a pair of antennae or an array of more than two antennae, the injection site preferably remains open or available for visualization and/or palpation. The sensors and methods of the present invention readily afford such availability. As illustrated, for example, in FIGS. 2, 3, 4A and 5, a plurality of antennae can be placed on the subject/patient in a disconnected state. However, it is often desirable to generally maintain a predetermined distance between antennae. In that regard, FIGS. 8A through 8D illustrate a "bowtie" sensor 500 including a pair of antennae 400 that generally or approximately maintains a predetermined distance (or range of distances) between antennae 400 (as described in connection with FIGS. 7A and 7B), while (i) providing flexibility to conform to the patient's tissue (see, for example, FIG. 8D) and (ii) allowing access to vicinity of the detection area (for example, an injection site in an extravasation detection).

In that regard sensor 500 includes a sensor base or support 505 including a first expanded base member or section 510a and a second expanded base member or section 510b in which antennae 400 are seated. First base section 510a and second base section 510b are connected by a flexible bridge 520 that allows some bending and/or twisting of first base section 510a and second base section 510b relative to each other to conform to, for example, a patient's arm or other region of interest. For a number of applications, sensor base 505 is thus preferably fabricated from a durable, flexible/resilient material having a relatively low dielectric constant. Many polymeric materials, such as, for example, polyurethane, are suitable for fabrication of sensor base 505. In several embodiments of the present invention, sensor base 505 was molded from an integral piece of polyurethane.

Bridge 520 maintains a separation between first base section 510a and a second base section 510b and the respective antennae 400 to ensure suitable coupling and to provide visual and tactile access to the injection site as, for example, defined by a catheter tip.

Figure 8D:
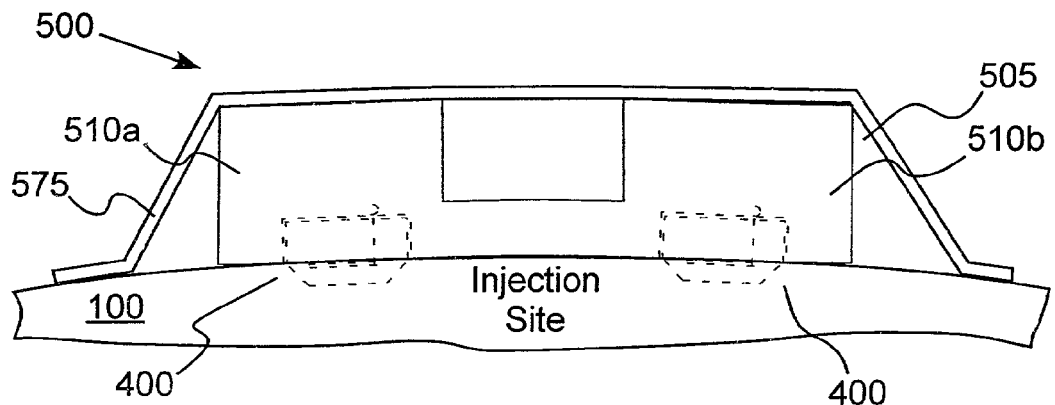
FIG. 8D illustrates a side view of the sensor of FIG. 8A coupled to a patient's arm.
Figure 8E:
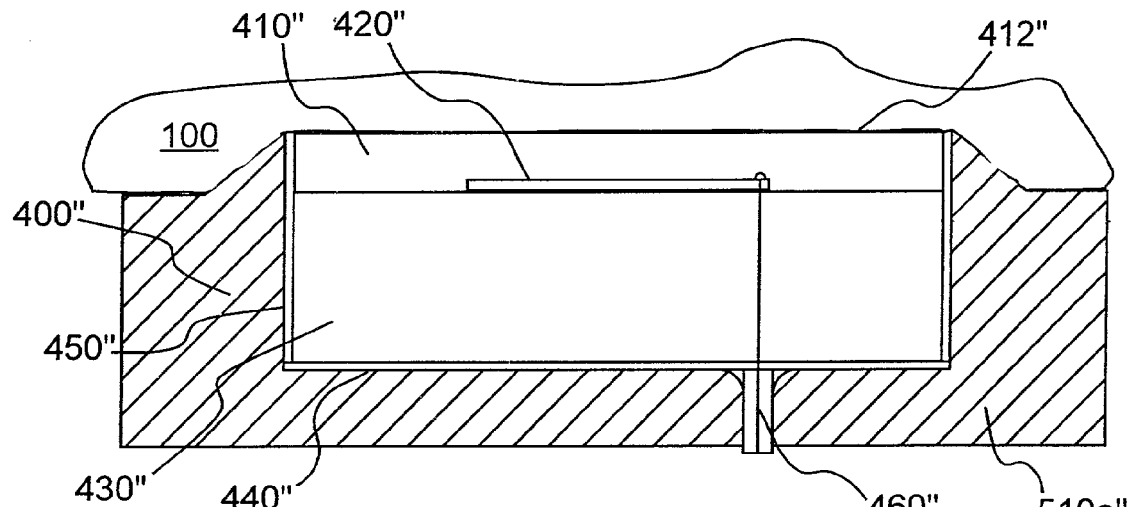
FIG. 8E illustrates a side, cross-sectional view of an embodiment of an antenna of the present invention positioned within a base member having a tapered profile to assist in conforming to tissue.

In addition to the use of a resilient base material it is also contemplated that base 505 can be fabricated of more rigid materials for given applications. It is further contemplated that the linear taper or smooth curvilinear surface described above relative to superstrate 410 can be formed on a sensor support, housing or base member 510a" (see FIG. 8E) rather than on a superstrate 410" to assist in conforming to tissue. Superstrate 410" in such an embodiment can be made generally flat or planar over its outward transmitting/receiving surface 412". If a support, housing or base member defines the taper, linear or curvilinear, or is generally flush with the face of an antenna such as antenna 400", shielding 450" for antenna 400" can be extended to the transmitting/receiving face 412" of superstrate 410" as illustrated in FIG. 8E.

Figure 9A:
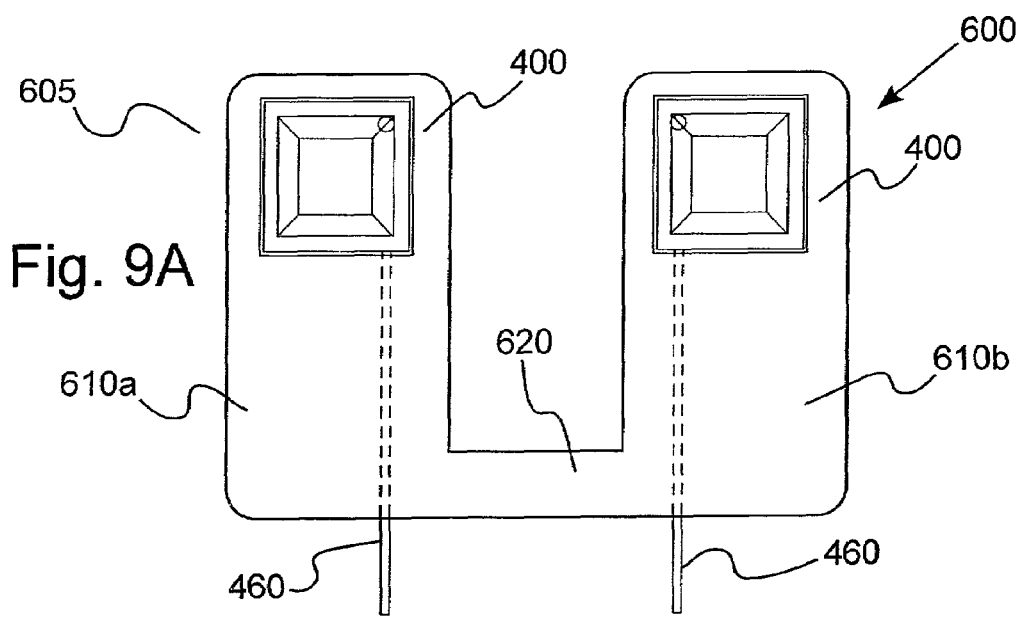
FIG. 9A illustrates a bottom view of a U-shaped sensor of the present invention including two antenna as illustrated in FIGS. 7A and 7B.
Figure 9B:
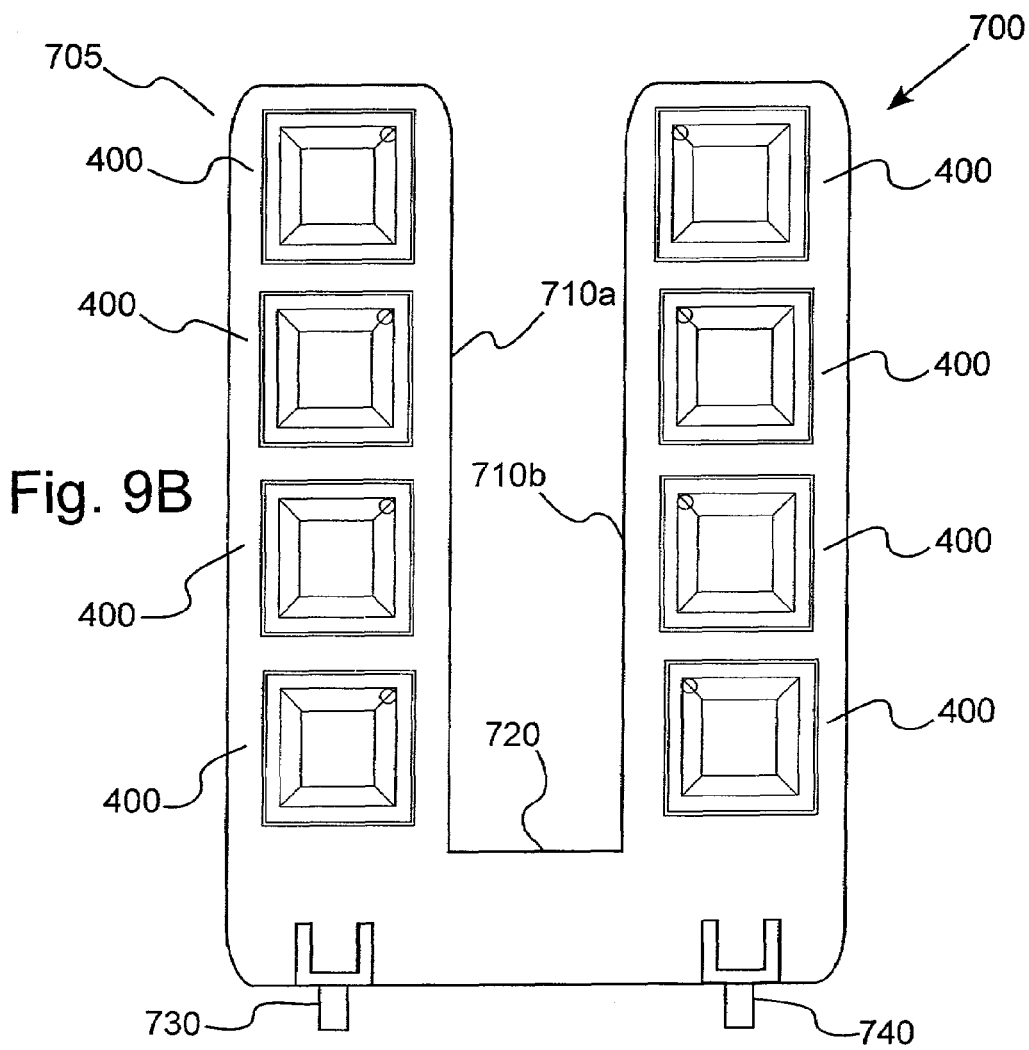
FIG. 9B illustrates a bottom view of a U-shaped sensor of the present invention including two linear arrays of four antennae as illustrated in FIGS. 7A and 7B.

FIGS. 9A and 9B illustrate alternative embodiments of sensors 600 and 700 of the present invention that (i) provide flexibility to conform to the patient's tissue and (ii) allow access to vicinity of the detection area (for example, an injection site in an extravasation detection). Sensor 600 of FIG. 9A is a U-shaped sensor including a sensor support or base 605 having a first base section 610a and a second base section 610b connected by a flexible bridge 620. As described above for sensor base 505, sensor base 605 is preferably fabricated from a resilient material such as a polyurethane. Each of first base section 610a and second base section 610b supports an antenna 400 as described above.

Sensor 700 of FIG. 9B is also a U-shaped sensor including a sensor support or base 705 having a first base section 710a and a second base section 710b connected by a flexible bridge 720. Sensor base 705 is also preferably fabricated from a resilient material such as a polyurethane. Each of first base section 710a and second base section 710b supports a linear array of an antenna 400. While all of antennae 400 of the linear arrays of FIG. 9B, are shown as being the same size, the sizes of the antennae can vary to provide various resonance frequencies of interest for the sensor.

Each of antennae 400 of sensor 700 can be connected to a power source/measurement device via individual wires or connective paths. Alternatively, integrated power/signal splitters, as known in the art, can be used. In that regard, as known in the RF communication arts, power splitters can be integrated into microstrip (planar) antenna designs, such that an array of antennas located on one layer can be fed through apertures located on another layer which are in turn fed by a power splitter and feeds on a third layer. This structure allows the simultaneous feeding of multiple transmitting antennas with one input signal or connection 730. Such a splitting method is also an effective method of combining signals from multiple receiving antennas into one signal or connection 740 to be processed. Adjustments in phasing for the antennas that make up the transmitting/receiving arrays can be done during the design phase, but will be fixed once the device is fabricated. This method can offer advantages in sensors of the present invention by, for example, improving directionality and therefore signal-to-noise ratio for the sensor.

Sensors of the present invention can, for example, also include opposing directional planar antennae. Directional planar antennae can be structured or fabricated similar to the antennae described above with an antenna element or resonant structure mounted between first and second substrates with shielding surrounding the antennae. Such directional planar antennae are, however, structured to emit microwaves from the ends or edges of the antennae rather than from the planar faces of the antennae. Such antennae, referred to as "edge-firing" antennas are well known in the art and include Yagi, Quasi-Yagi, Tapered Slot, Vivaldi Tapered Slot and others. Such sensors can, for example, include a mounting mechanism wherein the angular orientations of the antennae relative to each other can be varied. The specific angular orientations can be any reasonable value required for a given application and it is contemplated that different angular orientations can be used for each of the antennae.

EXPERIMENTAL EXAMPLES

1. Inorganic Phantom Experiments

Several experiments demonstrating the present invention were carried out using single and dual microstrip patch antenna configurations and an inorganic phantom to represent human tissue. Such inorganic phantoms provide the opportunity to accurately control both the position and amount of a simulated extravasation in an environment of generally known and simple dielectric properties (as compared to human tissue).

The microstrip antennae used in the studies were designed using Finite Difference Time Domain (FDTD) modeling techniques and were etched and fabricated in the laboratory. Standard equations, (generally available for well-understood geometries), were used to determine approximate dimensions required for the resonant structures of the various antennae studied in the present invention. Following that, substrate thickness was chosen to be a fraction of the wavelength corresponding to the primary resonant mode of the resonant structure. Finally, FDTD simulation techniques were used to refine dimensions and determine the best location for the feed connection. A FDTD software package available from Remcom Inc. of State College, Pennsylvania was used for the design of the antennae which were then etched and fabricated using well known laboratory techniques. As known in the art, moving a feed point outward towards the edge of a square resonant patch (to, for example, induce circular polarization) increases the impedance of the antenna. Ultimately an impedance similar to the driving circuitry is desired to maximize power transfer.

In general, below a frequency of approximately 1 GHz, the wavelength of electromagnetic energy begins to become sufficiently large that sensitivity to changes of interest in the tissue begins to decrease. Above approximately 10 GHz, the penetration of the waves into the tissue decreases, thereby decreasing sensing depth. Thus, the antennae used in the studies of the present invention were designed to resonate at an intermediate frequency of approximately 4 GHz.

Figure 11:
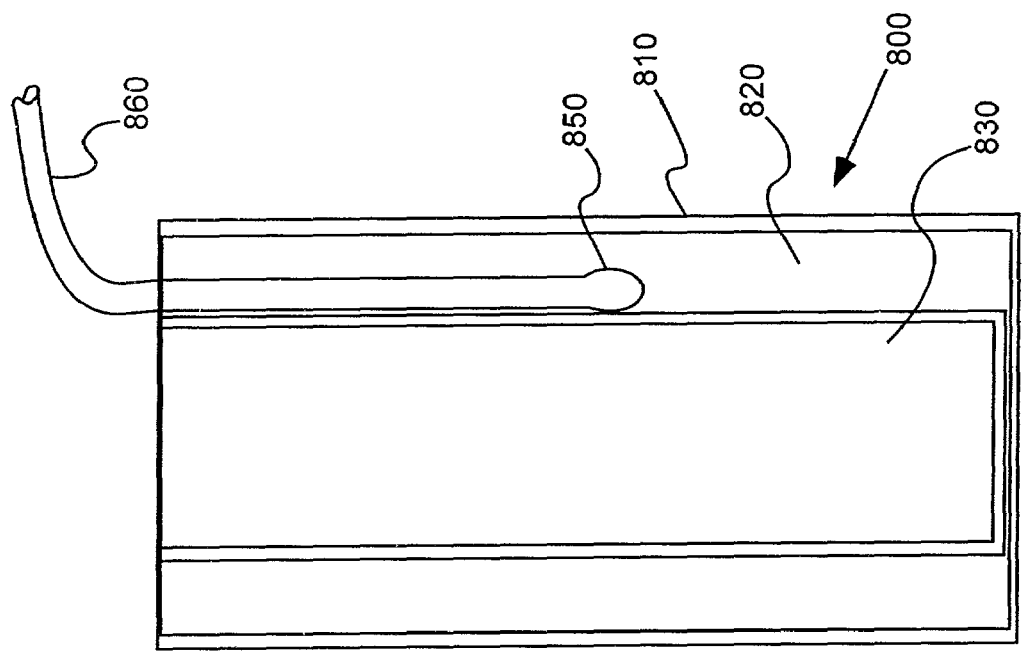
FIG. 11 illustrates a side, cross-sectional view of the phantom of FIG. 7.
Figure 10:
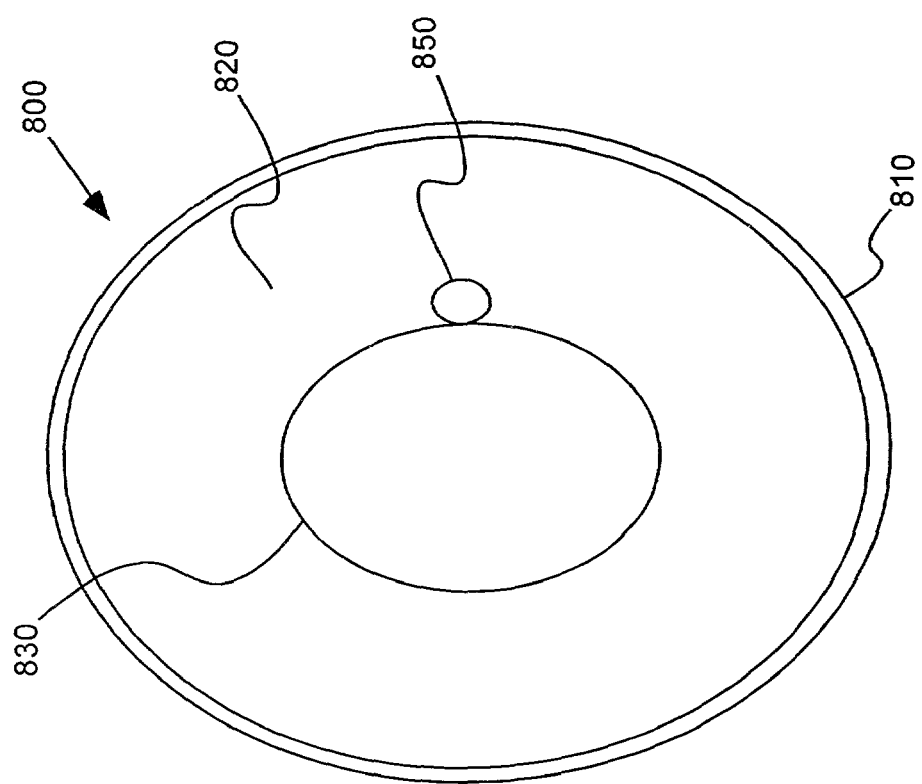
FIG. 10 illustrates a top view of an embodiment of a phantom used to model elevated or otherwise abnormal fluid levels in the human body.

The microstrip antennae included a ceramic type material coated with thin layers of copper for the resonant structure and ground plane as described above in connection with FIG. 6 and 7A–7D. Phantom 800 included emulated skin 810 (comprising carbon-loaded foam), an emulated fat layer 820 (comprising glycerin) and a movable, emulated muscle bundle 830 (comprising Ultravist 870 contrast medium or contrast agent available from Schering AG of Berlin, Germany) as illustrated in FIGS. 10 and 11. The emulation materials were chosen to approximate the dielectric properties of the material to be emulated.

Figure 12:
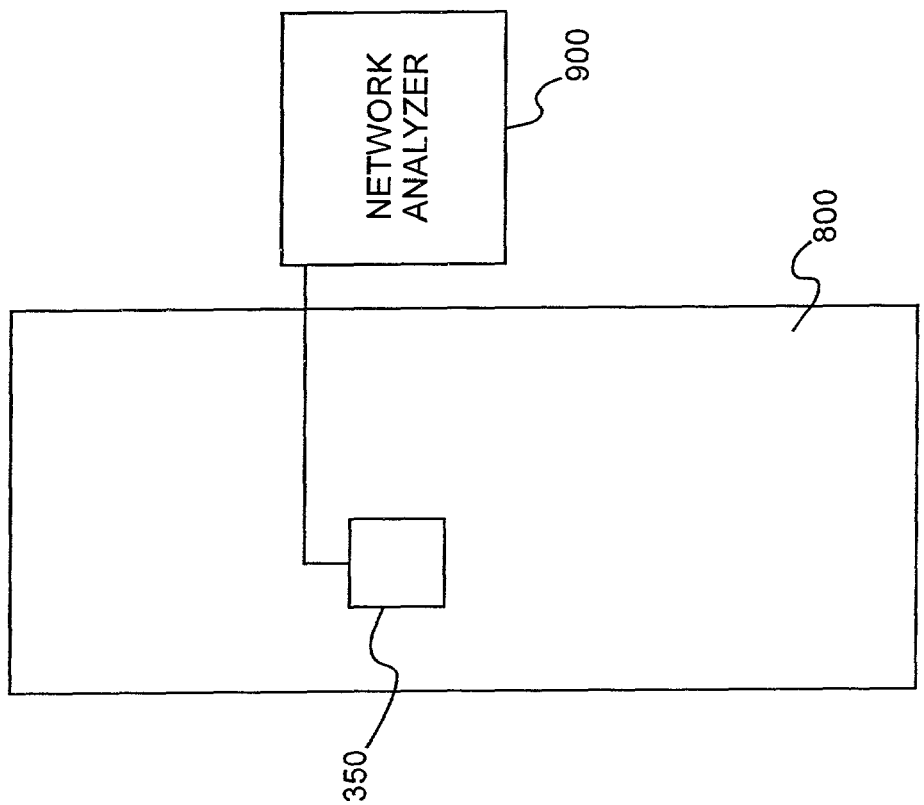
FIG. 12 illustrates an experimental setup in which a single antenna was used as both the transmitter and receiver.
Figure 13:
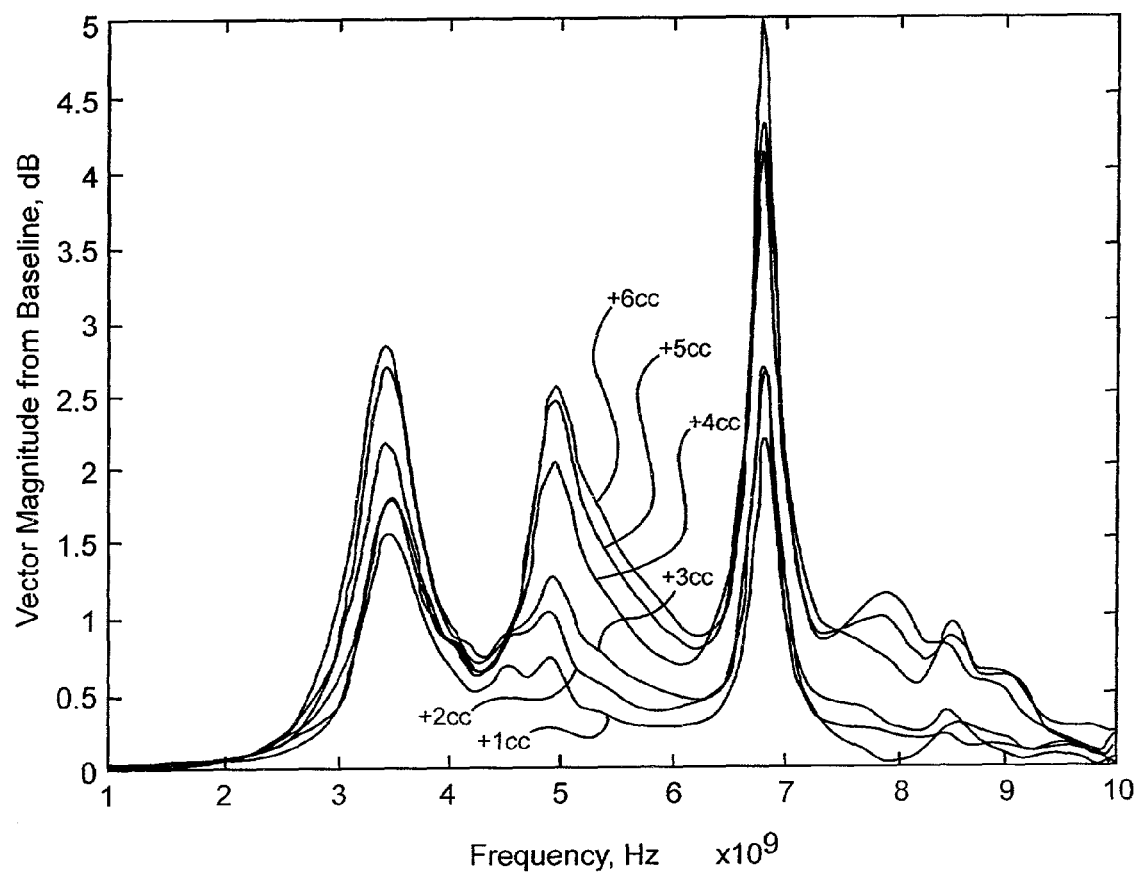
FIG. 13 the effect of increasing fluid level on the received signal in the setup of FIG. 9.

As illustrated in FIGS. 12 and 13, single and dual patch antenna configurations were arranged on phantom 800. An HP8510C network analyzer 900 was used to generate a source signal and to determine the response of antenna(e) 350 (see FIG. 6). Extravasation was emulated by filling a balloon 850 with Ultravist 870 contrast medium. Balloon 850 was filled via tubing 860 in fluid connection with a source of contrast medium (not shown). The thickness of emulated fat layer 820 in the configuration shown in FIGS. 10 and 11 was approximately 8 mm. Balloon 850 was filled with the contrast agent Ultravist 970 and placed between muscle layer 830 and skin layer 810.

Microstrip patch antennae 350 were designed to couple efficiently into tissue as described in connection with FIG. 6. By spacing resonating patch element 370 from skin layer 510 as illustrated in FIG. 6, one can reduce near-field loading. Furthermore, by using high-permittivity ceramic material in superstrate 360 to provide this non-conductive spacing and intrinsic impedance matching, energy coupling into tissue can be increased. In these experiments of the present invention, the substrate thickness was 2.5 mm and the superstrate thickness was 1.5 mm. The relative permittivity values at 5 GHz for each of the substrate and the superstrate were 10.2 and 20, respectively.

1A. Single Patch Antenna Experiments

In these experiments, a single antenna 350 was applied to phantom 800 generally directly over the extravasation site. The configuration is shown in FIG. 12. Emulated skin 810 and muscle bundle 830 were both in place during these experiments. $S_{11}$ measurements were made using network analyzer 900 to detect changes in the reflected energy created by antenna 300. The results from these experiments are shown in FIG. 13. The baseline in the experiments corresponded to balloon 850 filled with approximately 1–2cc of Ultravist 370.

1B. Dual Patch Antenna Experiments

Figure 14:
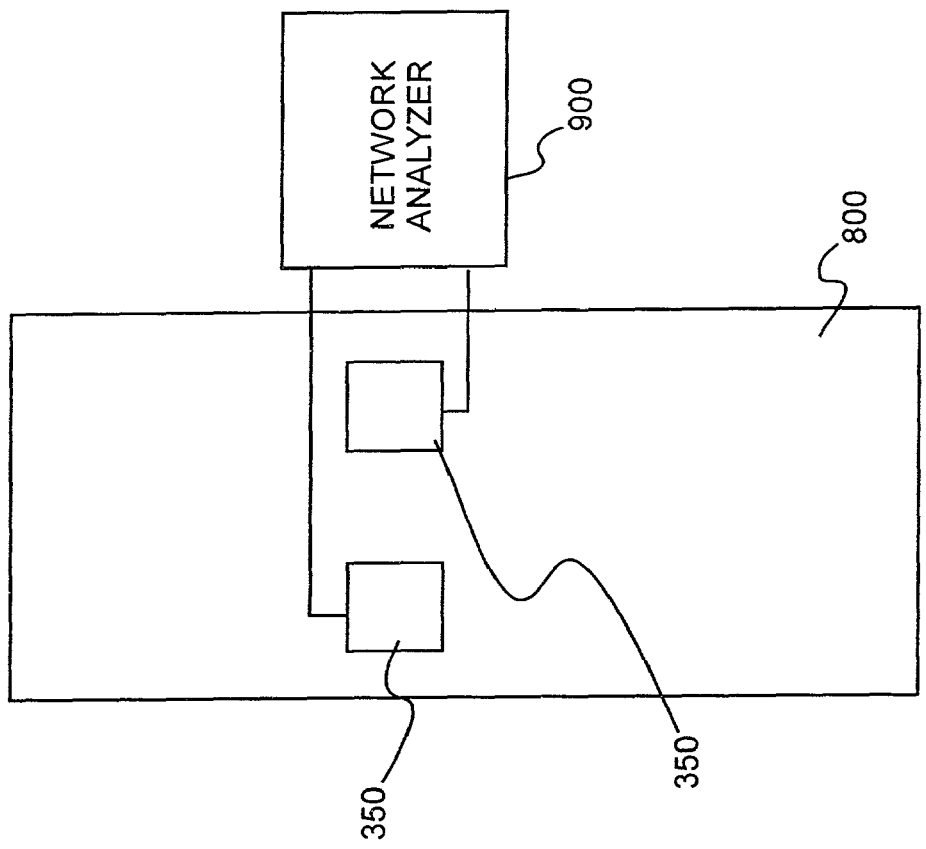
FIG. 14 illustrates and experimental setup in which one antenna was used as a transmitter and another antenna was used as a receiver.
Figure 15:
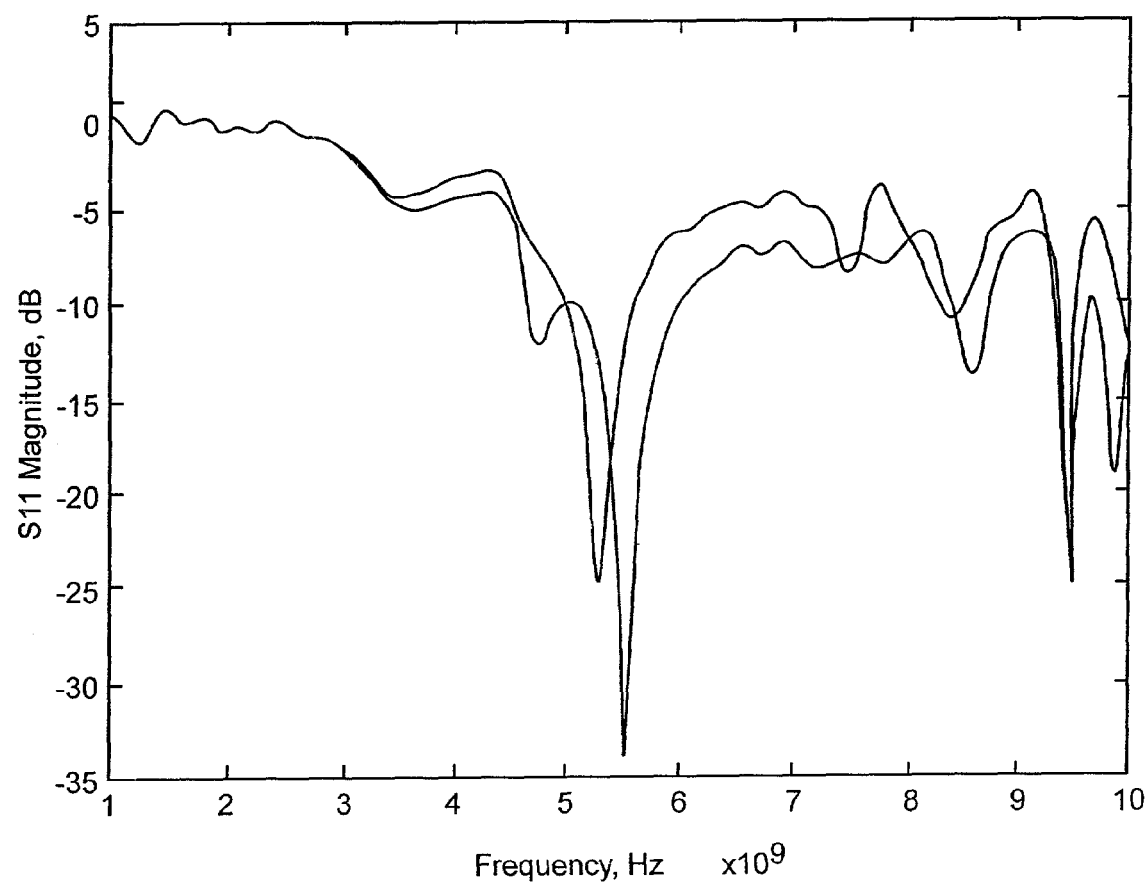
FIG. 15 illustrates a comparison of the resonance frequencies of the two antennae of FIG. 14.

The setup for the dual patch antenna configuration is shown in FIG. 14. First, $S_{11}$ measurements were made with each of patch antennae 350 to determine if antennae 350 resonated at similar frequencies and, therefore, coupled effectively. The results of these measurements are shown in FIG. 15. There was overlap in primary resonance modes for each antenna and sufficient $S_{21}$ coupling occurred, although the match was not optimized and can be readily improved to further increase coupling.

Figure 16:
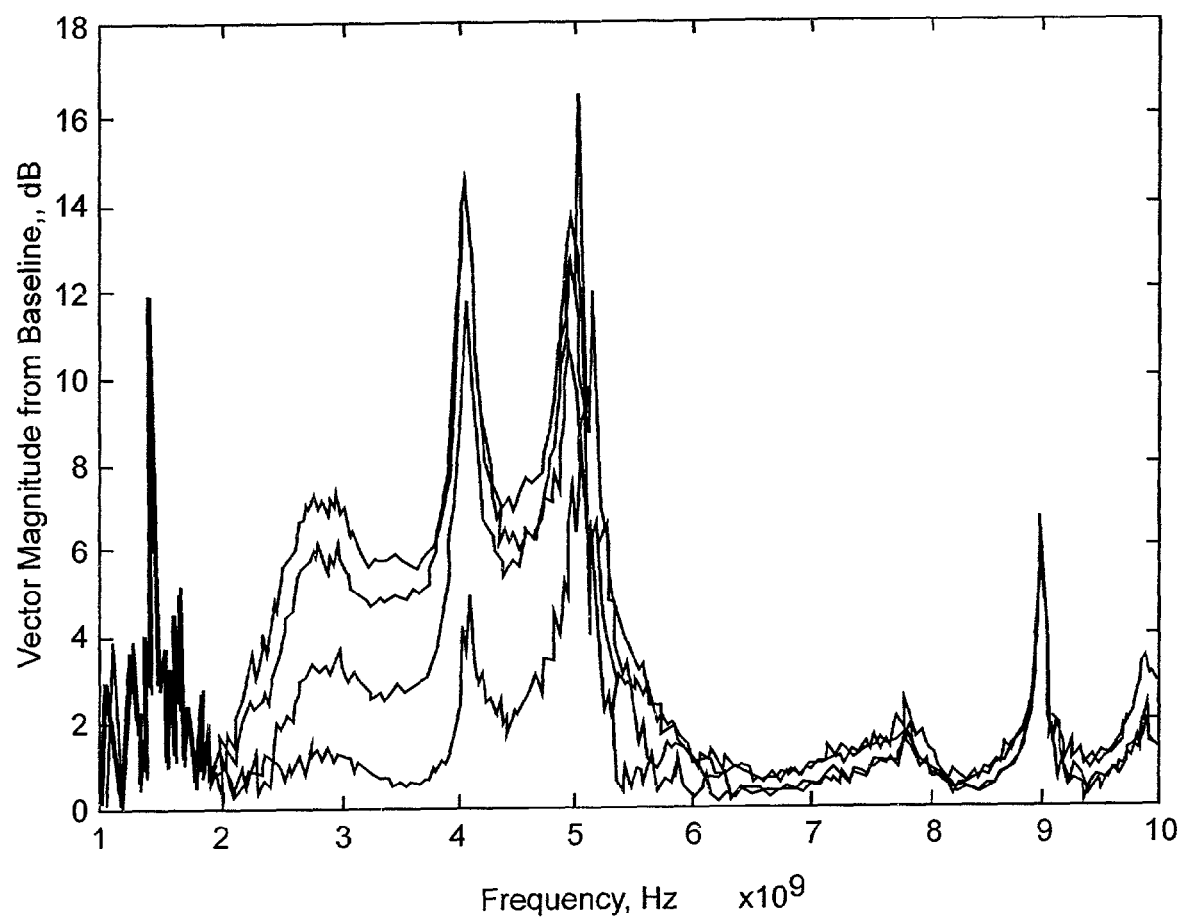
FIG. 16 the effect of increasing fluid level on the received signal in the setup of FIG. 14.

The separation between substrates 380 was approximately 1 cm, and the separation between active resonant elements 370 was approximately 2.5 cm. As clear to one skilled in the art, the substrate size can be reduced, and separation distance can be increased. Parameters such as directionality, tissue coupling, data processing and signal processing were not optimized in these experiments. The results for the dual antenna configuration are shown in FIG. 16. The baseline in this experiment corresponded to balloon 850 filled with approximately 1–2cc of Ultravist 870.

The results of each of the single antenna experiments and the dual antenna experiments indicate that elevated fluid levels are readily detectable using the detection systems of the present invention by comparison of a measured signal to a reference signal.

2. Organic Phantom Experiments

Although the inorganic phantom experiments described above, indicate the sensitivity of the sensors of the present invention to even slightly elevated fluid levels, emulation of the "lossy" dielectric nature of human skin using synthetic, inorganic materials is difficult. Thus, further experiments were conducted on organic phantoms to confirm the sensitivity of the sensors of the present invention to elevated or changing fluid levels in organic tissue. In these experiments, chicken skin/tissue was chosen as a model for human skin/tissue on the basis of similarity in permittivity between chicken tissue and human tissue, as determined by experiments conducted by the present inventors. In general, human skin varies in thickness from approximately 0.6 to 1.0 mm whereas chicken skin is approximately 0.4 mm thick. Experiments were thus performed with chicken phantoms having a single skin layer and a double skin layer (to better emulate human skin).

In several experiments on chicken skin/tissue, bowtie sensors 500 were used to measure change during simulated extravasation using Ultravist contrast medium. In several sensors 500 used in the studies, the spacing between the antennae 400 was approximately 1.5 cm. Inner corner feeds were used to induce circular polarization. The substrate thickness was approximately 2.5 mm. The superstrate thickness (the distance between resonant patch 410 and the forward surface plateau of superstrate 420 was approximately 1.25 mm. Resonant structure 410 was square with a side length and width of approximately 8 mm. Margin widths d were approximate 2 mm. Taper angle θ of superstrate 420 was approximately 30°.

Figure 17:
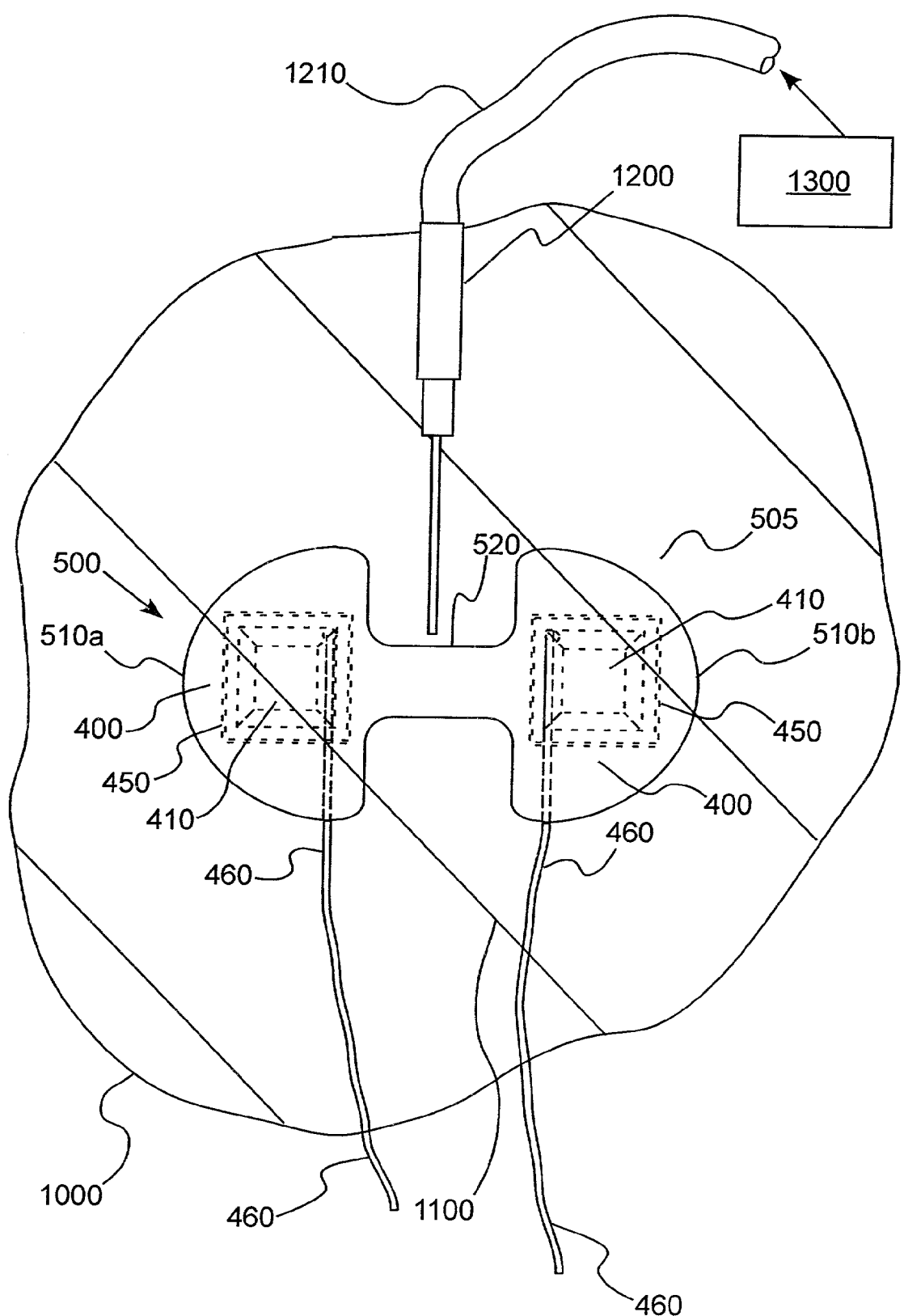
FIG. 17 illustrates the sensor of FIG. 8A in connection with a chicken phantom.

FIG. 17 illustrates attachment of sensor 500 to a chicken phantom 1000. Chicken phantom 1100 was wrapped tightly in plastic wrap 1100 for purposes of sanitation and to assist in maintaining the shape thereof. Sensor 500 was positioned on top of the plastic wrap 1100. Double sided adhesive tape 475 (see FIG. 7B), available from 3M under product number/name 1512, was applied to the bottom of sensor 500 before coupling to chicken phantom 1000. In some studies, super glue was also placed between double-sided tape 475 and plastic wrap 1100. Adhesive tape 575 (see FIG. 8D) was placed over sensor 500 to secure sensor 500 to chicken phantom 1000. Ultravist contrast medium was injected/extravasated into chicken phantom 1000 via a catheter 1200 connected to a VISTORON CT® injector 1300 available from Medrad, Inc. of Indianola, Pennsylvania via flexible tubing 1210.

Figure 18:
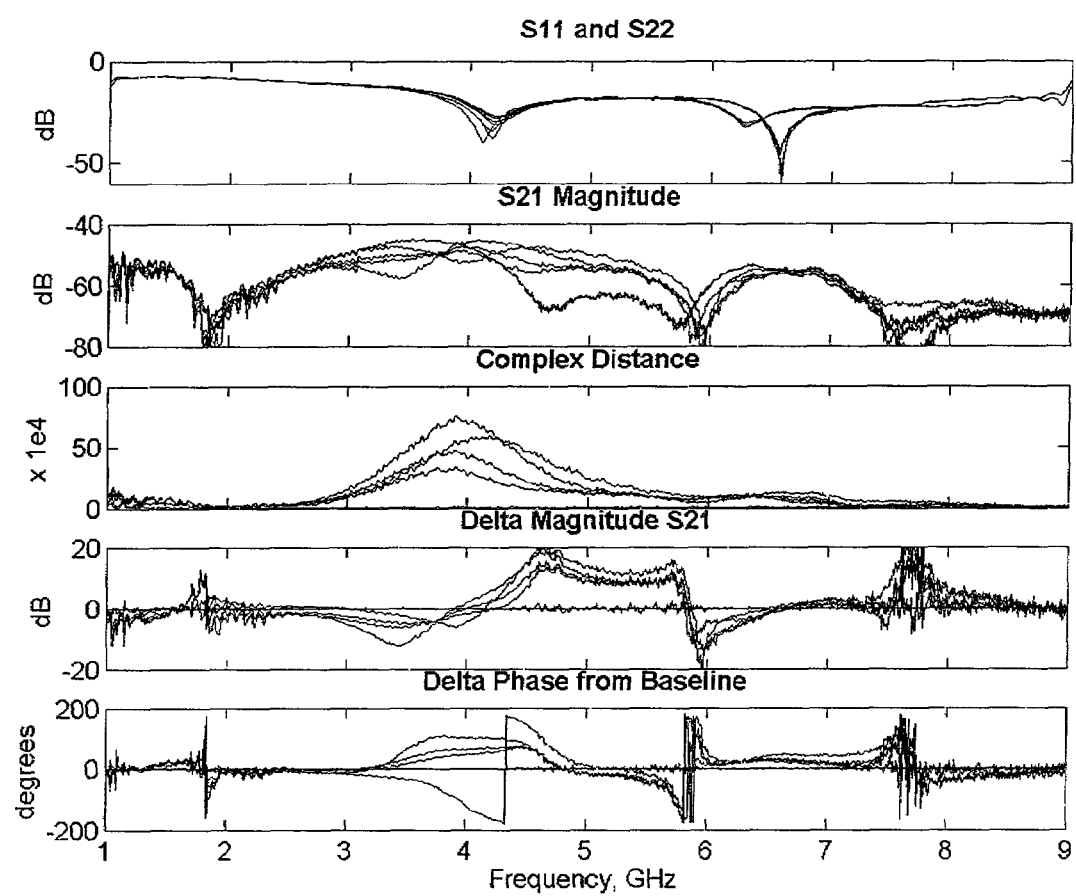
FIG. 18 illustrates signal data resulting from extravasation studies on a single-skinned chicken phantom.

Use of injector 1300 enabled accurate control of flow rate and volume of injected contrast medium. Contrast medium was injected at a flow rate of 2.5 cc/sec up to a volume of 10 cc. FIG. 18 illustrates data in several forms taken over a frequency range of 1 to 9 GHz from a single-skin chicken phantom using sensor 500 as described above. In that regard, FIG. 18 sets forth $S_{11}$ and $S_{22}$ data, $S_{21}$ magnitude data, complex distance data, $S_{21}$ delta magnitude data and delta phase from baseline data.

Of the above manners of expressing measured signal data, complex distance is believed to provide a direct relationship between extravasated volume and output. Other calculations that exhibit relationships to extravasation or fluid level change include, but are not limited to, changes from reference (baseline) in $S_{21}$ magnitude and $S_{21}$ phase. FIGS. 19A–19C illustrate complex distance as a function of frequency and volume injected in the upper graphs. The lower graphs of FIGS. 19A–C set forth the maximum complex distance over the measured range frequencies as a function of volume.

Figure 20:
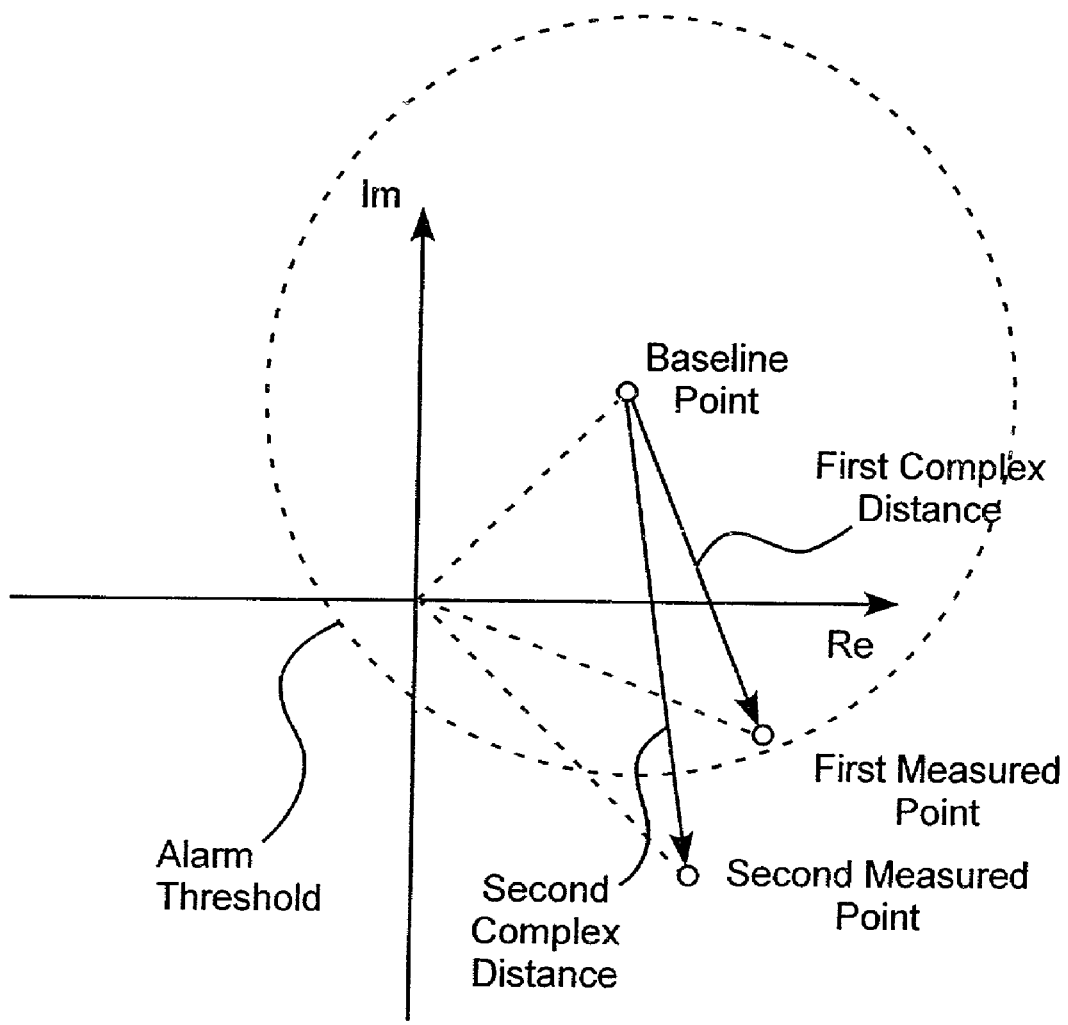
FIG. 20 illustrates a graphical representation of complex distance.

FIG. 20 provides a graphic illustration of a complex distance algorithm used in the studies of the present invention at a single frequency. The algorithm utilizes both magnitude and phase information and enhances frequency regions where signal coupling is strong. In one embodiment of the algorithm, a baseline signal (corresponding to 0 cc of injected contrast medium) was first measured at each frequency of interest. The magnitude and phase data was converted to complex form (that is, x+yi) and processed as illustrated in FIG. 20, wherein the real (Re) portion of the data is plotted against the imaginary (Im) portion. The complex distance corresponding to a particular data measurement is defined as the scalar distance between the baseline measurement and that measurement as illustrated in FIG. 20. An alarm threshold can, for example, be defined by a radius of complex distance around a baseline point (see dashed circular line in FIG. 20). As discussed above, baseline points can be reestablished throughout a study.

Furthermore, the algorithm in another embodiment includes a calculation of the area under the complex distance curve across a frequency range of interest. This calculation yields one number that can then be compared to a reference (baseline) number found with the same technique (that is, by calculating the area under a baseline curve across the frequency range of interest). In other words, the complex distances at the various frequencies are calculated. At that step, instead of comparing each complex distance to the threshold at that point, one integrates all of the complex distances in the frequency range of interest (providing the area under the curve). The resultant sum is compared to a threshold number corresponding to the area under the baseline curve across the frequency range of interest. Under the algorithm of FIG. 20, a single complex distance at some frequency crossing the threshold could trigger an alarm. In the case of comparison of integrated areas, however, a sufficiently strong single complex distance or a group of such complex distances are required to create a sum/integral that exceeds a threshold value. It is also possible, for example, to accumulate individual "complex distance" comparisons with their corresponding thresholds and determine that an alarm will be indicated only if a predetermined number of the "complex distances" have exceeded their thresholds.

It has been found that variation in the reference signal between humans and among different anatomical sites on the same human can lead to differing complex distance calculations for similar changes in the underlying tissue. Thus, for a given volume of extravasation in, for example, two different tissue anatomies, the complex distance calculation may yield significantly different values. To correct for such differences, the complex distance algorithm described above was altered by adding a step wherein the reference (baseline) $S_{21}$ magnitude curves were normalized. This result was achieved by simply multiplying every point in the reference $S_{21}$ curve by a factor to cause the peak value (or area under the curve) to equal one and then multiplying all subsequent measurement curves (curves created in a detection mode) by the same factor. This technique has been found to cause complex distance values to become more consistent when similar subcutaneous tissue changes occur in two different human subjects or in different anatomical sites on the same human.

FIGS. 19A and 19B correspond to experiments with double skin chicken phantoms 1000, while FIG. 19C corresponds to an experiment with a single skin chicken phantom 1000. The data of FIG. 18 and FIG. 19C are taken from the same experiment.

In FIG. 19A a gradual signal increase is observed as the volume of contrast medium injected increases. In FIG. 19B, a signal plateau was reached at injection of approximately 2 cc of contrast medium, indicative of signal saturation in the field of the sensor. In FIG. 19C, the signal increases to a maximum at approximately 4 cc of injected contrast medium and then subsequently decreases as more contrast medium is injected. It is believed, that tissue rupture may have led to dissipation of contrast medium from the tissue in the field of sensor 500 in the experiment of FIGS. 18 and 19C. FIGS. 19A through 19C indicate that the sensors of the present invention are sensitive to even small volumes of fluid in organic tissue. Moreover, it is possible that even information regarding the nature of, for example, an extravasated bolus of fluid can be provided by the sensors of the present invention. In that regard, the shape of the complex distance curve can, for example, indicate whether the fluid is pooled in the field of the sensor or dissipated therefrom.

3. Human Subject Experiments

Sensor 500 was also studied in several experiments with human subjects. In several such studies, signal output was measured at six different sites (for example, side, abdominal, and upper forearm areas), having varying fat layer thickness as determined by skin fold measurements. Such measurements indicated fat layers of 2.5, 3, 4, 5, 8 and 12 mm.

Figure 21A:
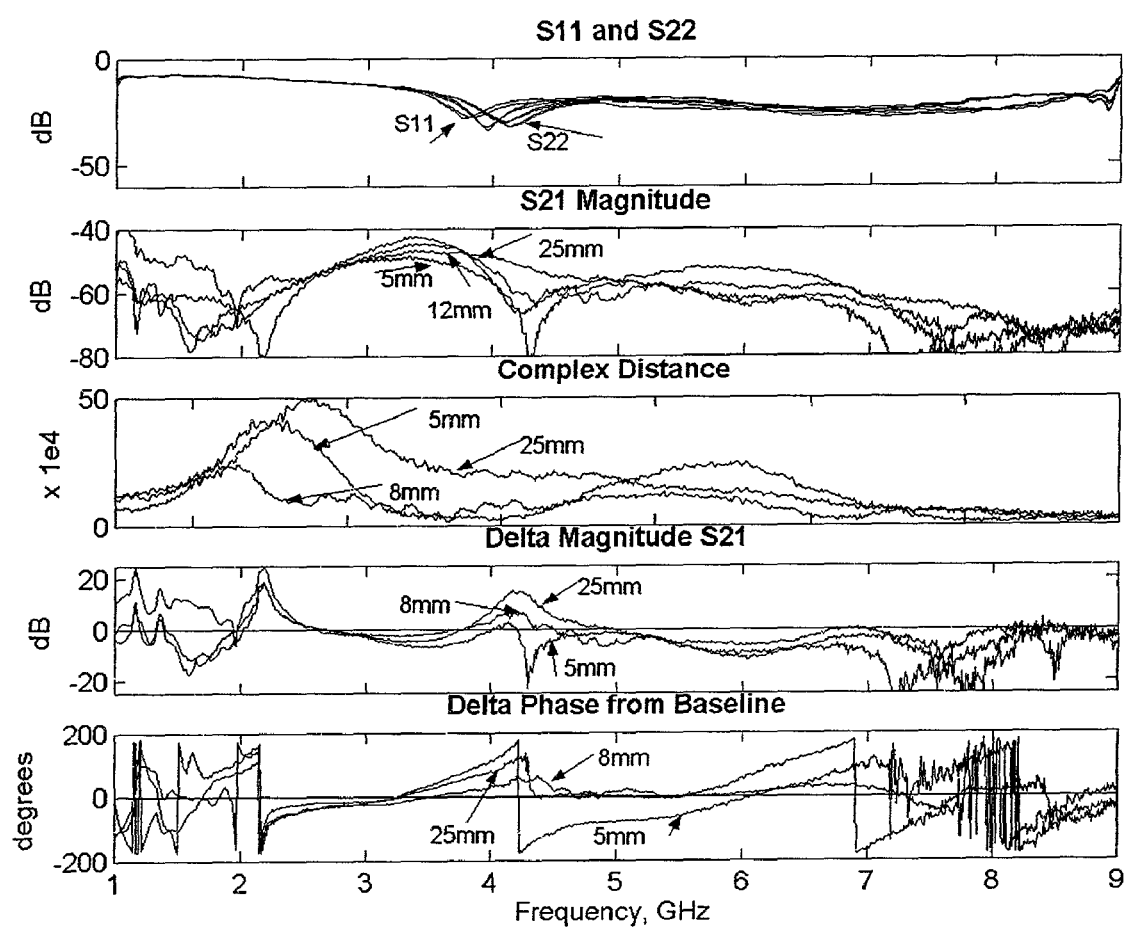
FIG. 21A illustrates signal data resulting from studies using the sensor of FIG. 8A on a human subject on areas of varying fat layer thickness.
Figure 21B:
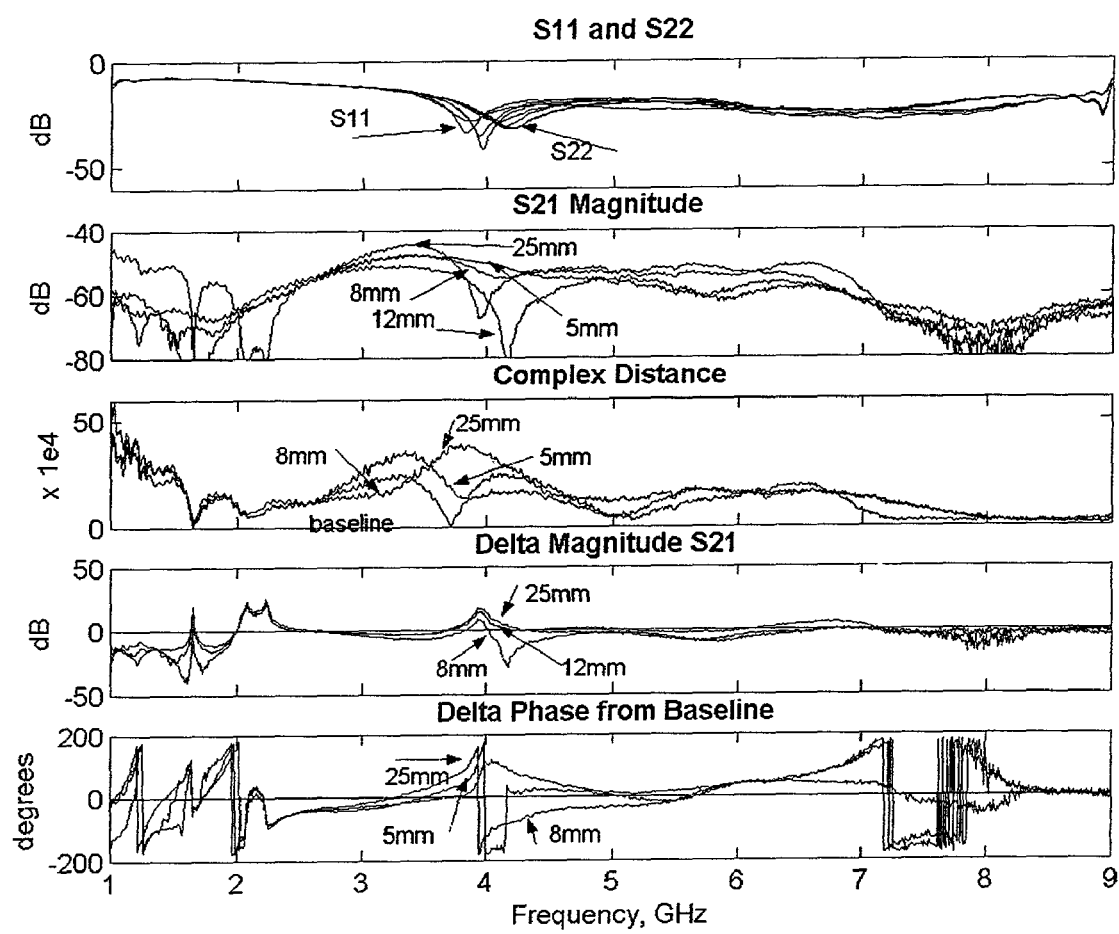
FIG. 21B illustrates signal data resulting from studies using the sensor of FIGS. 8A on another human subject on areas of varying fat layer thickness.

FIGS. 21A and 21B set forth $S_{11}$ and $S_{22}$ data, $S_{21}$ magnitude data, complex distance data, $S_{21}$ delta magnitude data and delta phase from baseline data for each of the fat layer thicknesses over a frequency range of approximately 1 to 9 GHz in two studies. The data demonstrate good skin and fat penetration of the energy of sensor 500 into human tissue at all the fat thicknesses studied.

The effect of patient motion on the output signal of sensor 500 was also studied. In these experiments, the underside of sensor 500, including antennae 400 was covered with double-sided adhesive tape 475 as illustrated in connection with FIG. 7A. In several experiments, the double-sided tape was then placed in direct contact with the patients skin in the area of the antecubital fossa. Adhesive tape 575 was then placed over sensor 500. The subject's arm was strapped in a jig to limit certain arm movements and the subject was led through six different arm position. In position 1 or the baseline position, the subject extended his or her arm to a straight position with the palm open and facing inward. In position 2, the subject clenched his or her fist. In position 3, the subject bent his or her elbow approximately 45° inward and opened his or her hand. In position 4, the subject maintained the elbow angle of position 3 and clenched his or her fist. In position 5, the subject maintained the elbow angle of positions 3 and 4 and supanated the wrist. In position 6, the arm was straightened and the wrist flexed.

Figure 22A:
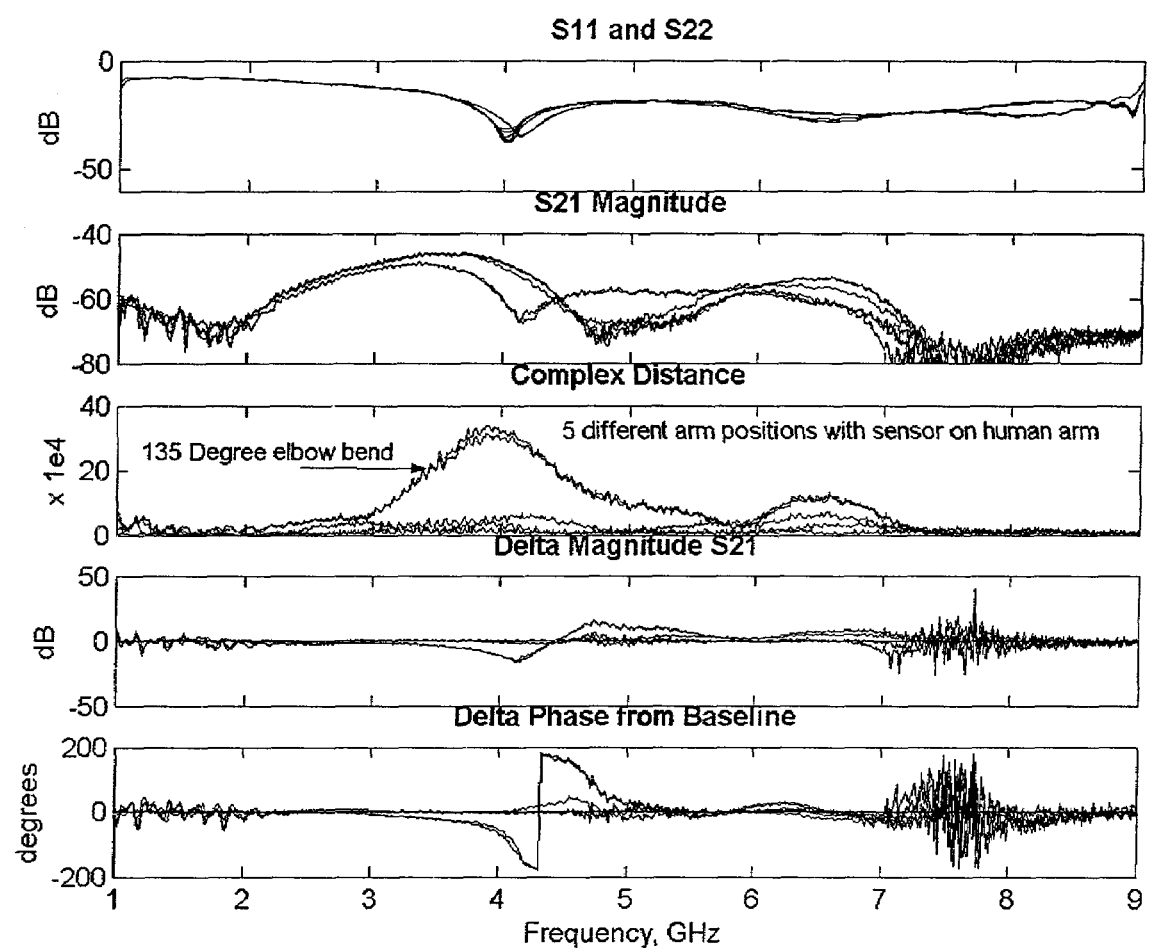
FIG. 22A illustrates signal data resulting from studies using the sensor of FIG. 8A on a human subject's arm at various arm positions.
Figure 22B:
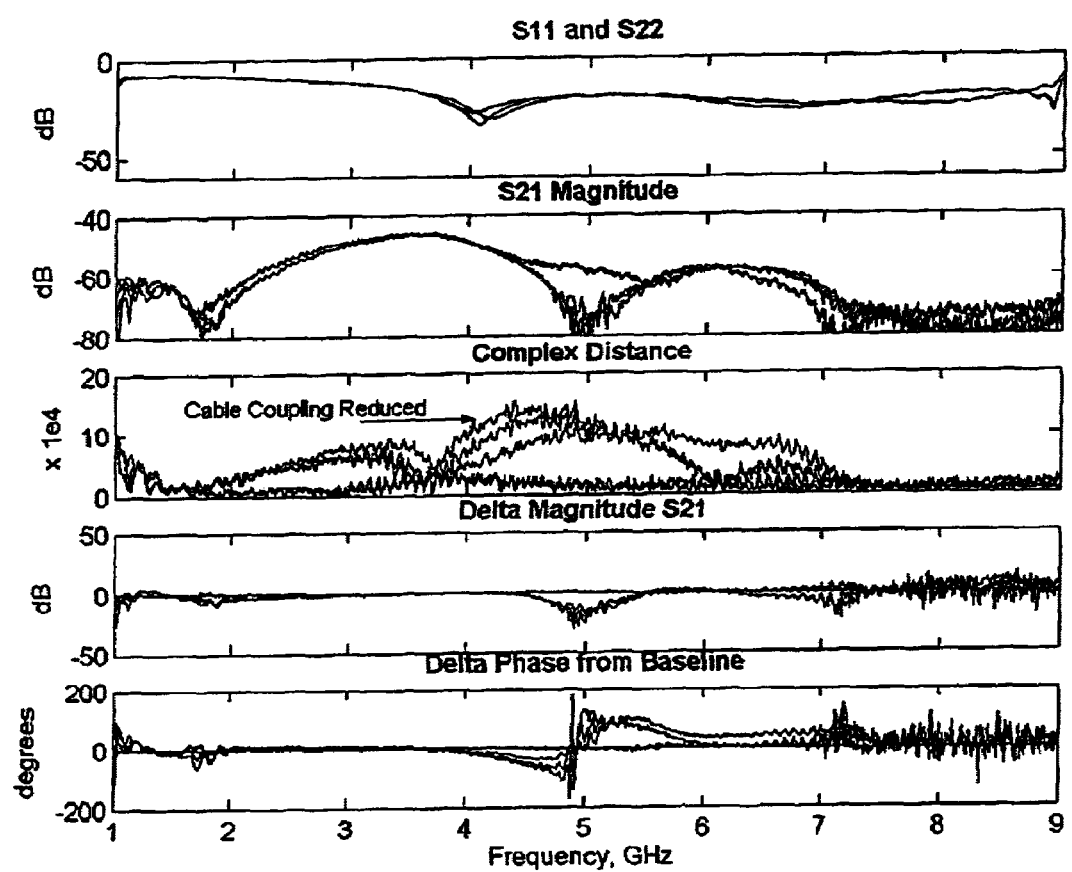
FIG. 22B illustrates signal data resulting from studies using the sensor of FIG. 8A on a human subject's arm at various arm positions wherein sensor cables were maintained in separation.

FIGS. 22A and 22B set forth $S_{11}$ and $S_{22}$ data, $S_{21}$ magnitude data, complex distance data, $S_{21}$ delta magnitude data and delta phase from baseline data for each of the above positions over a frequency range of approximately 1 to 9 GHz in two studies. The data demonstrate that the effect of patient motion on the output signal or motion artifact is not large as compared to the signal effect of fluid introduction found in the phantom studies. Thus, motion artifact will not present a substantial problem in, for example, detection of extravasation, and the effects of such artifacts can be further reduced via data manipulation such as averaging. In the studies of FIG. 22B, precaution was taken to prevent contact and excessive motion of the cable leads to antennae 400. Such precautions were found to decrease motion artifact as compared to the studies of FIG. 22A. It was determined that stray energy traveling on the outside of the cables can cross from one cable to the other and back down to the opposite antenna(s). In this scenario, motion of the cables will impact this stray energy and therefore its impact on the measurement signal. Furthermore, stray energy emitted by the transmitting antenna(s) can be reflected by nearby moving body parts such that the amount of stray energy scattered to the receiving antenna(s) can vary and impact the measured signal. Techniques such as proper shielding to minimize stray energy leakage and reception are therefore desirable. In addition to preventing contact and excessive motion of cable leads, it is also possible to user wireless transmission to reduce artifact.

Although the present invention has been described in detail in connection with the above embodiments and/or examples, it is to be understood that such detail is solely for that purpose and that variations can be made by those skilled in the art without departing from the invention. The scope of the invention is indicated by the following claims rather than by the foregoing description. All changes and variations which come within the meaning and range of equivalency of the claims are to be embraced within their scope.

What is claimed is:

1. A method of detecting a change in the level of fluid in tissue of a body comprising the steps of:
applying electromagnetic energy in the frequency range of greater than 1.5 GHz to approximately 30 GHz to a first volume of the body over a period of time;
measuring a resultant signal; and
comparing the signal to a reference signal to determine if fluid level in the tissue has changed during the period of time.

2. The method of claim 1 wherein the electromagnetic energy is in the frequency range of approximately 2 GHz to approximately 10 GHz.

3. The method of claim 1 wherein the electromagnetic energy is in the frequency range of approximately 2 GHz to approximately 5 GHz.

4. The method of claim 1 wherein the reference signal is a baseline signal measured in the first volume of the body.

5. The method of claim 4 wherein the step of comparing the measured signal to the baseline measurement includes the step of calculating a complex distance between the measured signal and the baseline measurement.

6. The method of claim 4 wherein an area under a complex distance curve across a frequency range of interest is calculated, and the calculated area is compared to the area under a baseline curve over the frequency range of interest.

7. The method of claim 4 wherein the step of applying electromagnetic energy includes the step of coupling a transmitter with skin.

8. The method of claim 7 wherein the transmitter includes a generally planar resonant structure.

9. The method of claim 8 wherein the transmitter includes a superstrate adjacent the resonant structure having an impedance suitable to couple with skin.

10. The method of claim 9 wherein an outward side of the transmitter superstrate is shaped to conform to skin.

11. The method of claim 10 wherein the periphery of the outward side of the transmitter superstrate is tapered.

12. The method of claim 7 further comprising the step of coupling a receiver with the skin.

13. The method of claim 12 wherein the transmitter is an antenna including a first generally planar resonant structure and the receiver is an antenna including a second generally planar resonant structure, the transmitter being connected to a first base member and the receiver being connected to a second base member, the first base member and the second base member being connected by a flexible bridge.

14. The method of claim 12 wherein the receiver includes a generally planar resonant structure.

15. The method of claim 14 wherein the receiver includes a superstrate adjacent the resonant structure having an impedance suitable to couple with skin.

16. The method of claim 15 wherein an outward side of the receiver superstrate is shaped to conform to skin.

17. The method of claim 16 wherein the periphery of the outward side of the receiver superstrate is tapered.

18. The method of claim 1 wherein the reference signal is produced by applying electromagnetic energy in the frequency range of greater than 1.5 GHz to approximately 30 GHz to the tissue in a second volume of the body.

19. The method of claim 18 wherein tissue in the second volume of the body is similar in electromagnetic properties to tissue in the first volume of the body.

20. The method of claim 1 wherein the reference signal is developed by applying electromagnetic energy in the frequency range of greater than 1.5 GHz to approximately 30 GHz to tissue of a plurality of bodies.

21. The method of claim 1 wherein the measured signal is a function of the permittivity of tissue in the first volume of the body or the permeability of tissue in the first volume of the body.

22. The method of claim 1 wherein the change in fluid level in the tissue occur over a period of approximately one second to three days.

23. The method of claim 1 wherein the fluid is a body fluid.

24. The method of claim 23 wherein the change in the level of the fluid is caused by edema.

25. The method of claim 23 wherein the change in the level of the fluid is caused by a hematoma.

26. The method of claim 1 wherein the fluid is a fluid introduced to the body.

27. The method of claim 26 wherein the fluid is introduced by injection, infusion or intravenous drip.

28. A method of detecting extravasation of a fluid injected into a vascular structure of a body in tissue outside of the vascular structure, comprising the steps of:
applying electromagnetic energy in the frequency range of approximately 300 MHz to approximately 30 GHz to a first volume of the body during a period of time in which a fluid is injected into the vascular structure;
measuring a resultant signal; and
comparing the signal to a reference signal to determine fluid level in the tissue has changed during the period of time.

29. A method of detecting extravasation of a fluid injected into a vascular structure of a body in tissue outside of the vascular structure, comprising the steps of:
placing at least one antenna in operative connection with the skin of the body;
applying electromagnetic energy in the frequency range of aporoximately 300 MHz to approximately 30 GHz to a first volume of the body using the antenna;
injecting the fluid into the vascular structure;
measuring a returned signal; and
comparing the signal to a reference signal to determine if extravasation has occurred.

30. The method of claim 29 wherein the electromagnetic energy is in the frequency range of greater than 1.5 GHz to approximately 30 GHz.

31. The method of claim 29 wherein the electromagnetic energy is in the frequency range of approximately 1 GHz to approximately 10 GHz.

32. The method of claim 29 wherein the electromagnetic energy is in the frequency range of approximately 2 GHz to approximately 5 GHz.

33. The method of claim 29 wherein the reference signal is a baseline signal measured in the first volume.

34. The method of claim 33 wherein the step of comparing the measured signal to the baseline measurement includes the step of calculating a complex distance between the measured signal and the baseline measurement.

35. The method of claim 33 wherein an area under a complex distance curve across a frequency range of interest is calculated, and the calculated area is compared to the area under a baseline curve over the frequency range of interest.

36. The method of claim 33 wherein at least one transmitter antenna to transmit electromagnetic energy into the first volume of the body is placed in operative connection with the skin and at least one receiver antenna to measure a resultant signal is placed in operative connection with the skin.

37. The method of claim 36 wherein the transmitter antenna includes a generally planar resonant structure.

38. The method of claim 37 wherein the transmitter antenna includes a superstrate adjacent the resonant structure having an impedance suitable to couple with skin.

39. The method of claim 38 wherein an outward side of the transmitter antenna superstrate is shaped to conform to skin.

40. The method of claim 39 wherein the periphery of the outward side of the transmitter antenna superstrate is tapered.

41. The method of claim 36 wherein the receiver antenna includes a generally planar resonant structure.

42. The method of claim 41 wherein the receiver antenna includes a superstrate adjacent the resonant structure having an impedance suitable to couple with skin.

43. The method of claim 42 wherein an outward side of the receiver antenna superstrate is shaped to conform to skin.

44. The method of claim 43 wherein the periphery of the outward side of the receiver antenna superstrate is tapered.

45. The method of claim 36 wherein the transmitter antenna is connected to a first base member and the receiver antenna is connected to a second base member, the first base member and the second base member being connected by a flexible bridge.

46. The method of claim 45 wherein a site at which the injection occurs remain open for palpation or visualization during the injection.

47. The method of claim 29 wherein the reference signal is produced by applying electromagnetic energy to tissue in a second area of the body.

48. The method of claim 47 wherein the tissue in the second area is similar in electromagnetic properties to the tissue in the first area.

49. The method of claim 29 wherein the reference signal is developed by applying electromagnetic energy to tissue of a plurality of bodies in which there is no extravasation.

50. The method of claim 29 wherein the measured signal is a function of the permittivity of the tissue or the permeability of the tissue.

51. The method of claim 29 wherein a site at which the injection occurs remain open for palpation or visualization during the injection.

52. A method of detecting a change in the level of fluid in tissue in a body comprising the steps of:
transmitting electromagnetic energy in the frequency range of approximately 300 MHz to approximately 30 GHz in the vicinity of a surface of the body such that changes in the surface geometry of the surface resulting from a change in fluid level of underlying tissue affect a resultant signal;
measuring the resultant signal; and
comparing the resultant signal to a reference signal.

53. An injection system comprising:
an injector to inject a fluid into a vascular structure in a body;
at least a first transmitter including an antenna adapted to transmit electromagnetic energy in the frequency range of approximately 300 MHz to approximately 30 GHz to a first volume of the body;
at least a first receiver to measure a returned signal;
a memory storing a reference signal, the reference signal created by transmitting electromagnetic energy into the first volume of the body prior to an injection and measuring a resultant signal; and
a signal processor in communication with the first receiver and the memory, the processor comparing the returned signal to the reference signal to determine if the level of fluid in tissue outside the vascular structure has changed.

54. The system of claim 53 wherein the antenna is adapted to transmit electromagnetic energy in the frequency range of approximately 1.5 GHz to approximately 30 GHz.

55. The system of claim 53 wherein the antenna is adapted to transmit electromagnetic energy in the frequency range of approximately 2 GHz to approximately 10 GHz.

56. The system of claim 53 wherein the antenna is adapted to transmit electromagnetic energy in the frequency range of approximately 2 GHz to approximately 5 GHz.

57. The system of claim 53 wherein the reference signal is a baseline signal measured in the first volume of the body.

58. The system of claim 53 wherein the reference signal is produced by applying electromagnetic energy in the frequency range of greater than 1.5 GHz to approximately 30 GHz to the tissue in a second volume of the body.

59. The system of claim 53 wherein the antenna of the transmitter is adapted to be coupled with skin.

60. The system of claim 59 wherein the transmitter comprises a generally planar resonant structure.

61. The system of claim 60 wherein the transmitter comprises a superstrate adjacent the resonant structure having an impedance suitable to couple with skin.

62. The system of claim 53 wherein the receiver is adapted to be coupled with skin.

63. The system of claim 53 wherein the receiver comprises an antenna comprising a generally planar resonant structure.

64. The system of claim 63 wherein the receiver comprises a superstrate adjacent the resonant structure having an impedance suitable to couple with skin.

65. The system of claim 53 wherein the antenna of the transmitter comprises a first generally planar resonant structure and the receiver comprises an antenna comprising a second generally planar resonant structure, the transmitter being connected to a first base member and the receiver being connected to a second base member, the first base member and the second base member being connected by a flexible bridge.

66. The system of claim 53 wherein the measured signal is compared to the baseline measurement by calculating a complex distance between the measured signal and the baseline measurement.

67. The system of claim 53 wherein an area under a complex distance curve across a frequency range of interest is calculated, and the calculated area is compared to the area under a baseline curve over the frequency range of interest.

68. A system for injection of an injection fluid into a body comprising: a pressurizing chamber in which injection fluid is pressurized for injection into a vascular structure of a body; and an extravasation detector, the extravasation detector including at least a first transmitter including an antenna adapted to transmit electromagnetic energy in the frequency range of approximately 300 MHz to approximately 30 GHz to a first volume of the body; at least a first receiver to measure a returned signal; a memory storing a reference signal, the reference signal created by transmitting electromagnetic energy into the first volume of the body prior to an injection of fluid and measuring a resultant signal; and a signal processor in communication with the first receiver and the memory, the processor comparing the returned signal to the reference signal to determine if the level of fluid in tissue outside the vascular structure has changed.

69. The system of claim 68 wherein the antenna is adapted to transmit electromagnetic energy in the frequency range of approximately 1.5 GHz to approximately 30 GHz.

70. The system of claim 68 wherein the antenna is adapted to transmit electromagnetic energy in the frequency range of approximately 2 GHz to approximately 10 GHz.

71. The system of claim 68 wherein the antenna is adapted to transmit electromagnetic energy in the frequency range of approximately 2 GHz to approximately 5 GHz.

72. The system of claim 68 wherein the reference signal is a baseline signal measured in the first volume of the body.

73. The system of claim 68 wherein the reference signal is produced by applying electromagnetic energy in the frequency range of greater than 1.5 GHz to approximately 30 GHz to the tissue in a second volume of the body.

74. The system of claim 68 wherein the transmitter is adapted to be coupled with skin.

75. The system of claim 68 wherein the antenna of the transmitter comprises a generally planar resonant structure.

76. The system of claim 75 wherein the transmitter comprises a superstrate adjacent the resonant structure having an impedance suitable to couple with skin.

77. The system of claim 68 wherein the receiver is adapted to be coupled with skin.

78. The system of claim 68 wherein the receiver comprises an antenna comprising a generally planar resonant structure.

79. The system of claim 78 wherein the receiver comprises a superstrate adjacent the resonant structure having an impedance suitable to couple with skin.

80. The system of claim 68 wherein the antenna of the transmitter comprises a first generally planar resonant structure and the receiver comprises an antenna comprising a second generally planar resonant structure, the transmitter being connected to a first base member and the receiver being connected to a second base member, the first base member and the second base member being connected by a flexible bridge.

81. The system of claim 68 wherein the measured signal is compared to the baseline measurement by calculating a complex distance between the measured signal and the baseline measurement.

82. The system of claim 68 wherein an area under a complex distance curve across a frequency range of interest is calculated, and the calculated area is compared to the area under a baseline curve over the frequency range of interest.

83. A method of detecting a change in the level of fluid in tissue of a body comprising the steps of:
  applying electromagnetic energy in the frequency range of greater than 1.5 GHz to approximately 30 GHz to a first volume of the body using at least one antenna;
  measuring a resultant signal using at least one other antenna; and
  comparing the signal to a reference signal.

* * * * *

UNITED STATES PATENT AND TRADEMARK OFFICE
CERTIFICATE OF CORRECTION

PATENT NO. : 7,122,012 B2  Page 1 of 1
APPLICATION NO. : 10/206390
DATED : October 17, 2006
INVENTOR(S) : Chad Bouton et al.

It is certified that error appears in the above-identified patent and that said Letters Patent is hereby corrected as shown below:

Column 3
Line 57, replace "whole Fish" with --Whole Fish--.

Column 24
Claim 22, line 19, replace "occur" with --occurs--.
Claim 28, line 39, after "to determine" insert --if--.

Column 25
Claim 46, line 40, replace "remain" to --remains--.
Claim 51, line 56, replace "remain" to --remains--.

Signed and Sealed this

Thirtieth Day of January, 2007

JON W. DUDAS
*Director of the United States Patent and Trademark Office*